(12) United States Patent
Johnson et al.

(10) Patent No.: US 8,540,710 B2
(45) Date of Patent: Sep. 24, 2013

(54) METHODS AND APPARATUSES FOR TISSUE TREATMENT

(75) Inventors: Theodore C. Johnson, Ann Arbor, MI (US); Daniel J. Balbierz, Redwood City, CA (US); Robert M. Pearson, San Jose, CA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 13/609,369

(22) Filed: Sep. 11, 2012

(65) Prior Publication Data

US 2013/0006228 A1 Jan. 3, 2013

Related U.S. Application Data

(63) Continuation of application No. 12/178,684, filed on Jul. 24, 2008, which is a continuation of application No. 09/916,214, filed on Jul. 25, 2001, now Pat. No. 7,419,487.

(60) Provisional application No. 60/220,639, filed on Jul. 25, 2000.

(51) Int. Cl.
*A61B 18/14* (2006.01)

(52) U.S. Cl.
USPC .............................. 606/41; 607/101

(58) Field of Classification Search
USPC .................. 606/41, 42, 48–50; 607/100–102
See application file for complete search history.

(56) References Cited

U.S. PATENT DOCUMENTS

| | | | | |
|---|---|---|---|---|
| 5,458,597 | A * | 10/1995 | Edwards et al. | 606/41 |
| 5,536,267 | A * | 7/1996 | Edwards et al. | 606/41 |
| 5,728,143 | A * | 3/1998 | Gough et al. | 607/101 |
| 6,009,347 | A * | 12/1999 | Hofmann | 604/21 |
| 6,106,524 | A * | 8/2000 | Eggers et al. | 606/50 |
| 6,478,793 | B1 * | 11/2002 | Cosman et al. | 606/34 |
| 7,008,421 | B2 * | 3/2006 | Daniel et al. | 606/50 |

* cited by examiner

*Primary Examiner* — Michael Peffley
(74) *Attorney, Agent, or Firm* — Peter J. Flora

(57) ABSTRACT

Disclosed in the present application are devices for localized delivery of energy and methods of using such devices, particularly for therapeutic treatment of biological tissues. The disclosed methods may involve positioning and deploying the energy delivery members in a target site, and delivering energy through the energy delivery members. The disclosed devices may also be used to create a tissue tract within a biological tissue and to ablate the tissue tract.

25 Claims, 26 Drawing Sheets

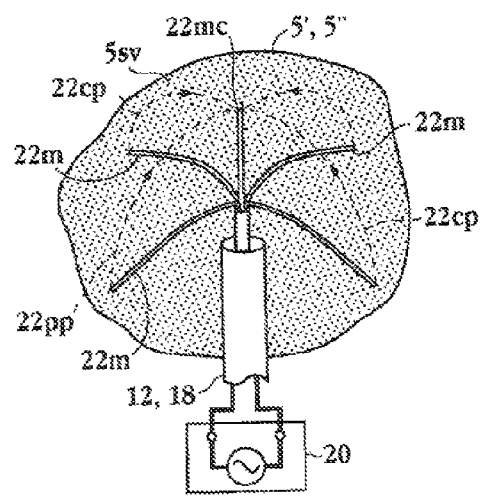
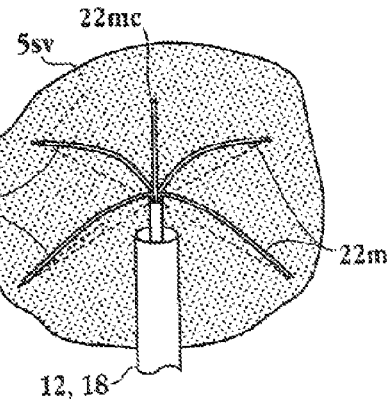
Fig. 4A
Fig. 4B
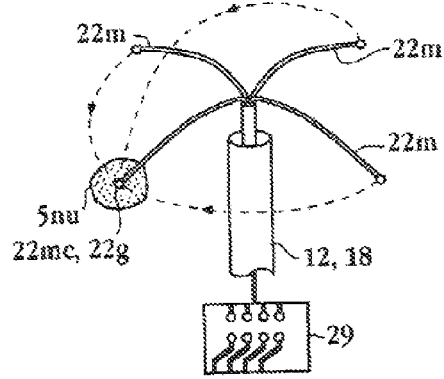
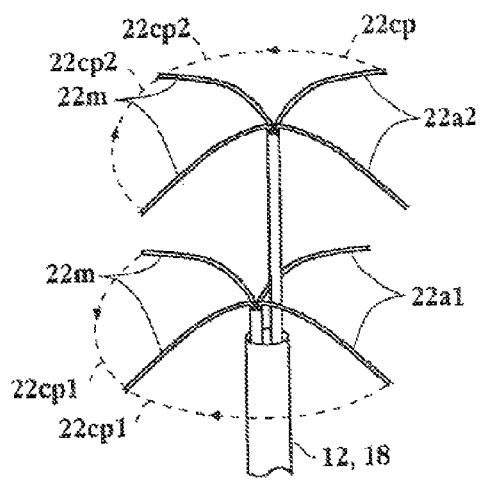
Fig. 4C
Fig. 4D

METHODS AND APPARATUSES FOR TISSUE TREATMENT

CROSS-REFERENCE TO RELATED APPLICATIONS

This is a continuation of U.S. application Ser. No. 12/178,684, filed Jul. 24, 2008, which is a continuation of U.S. Pat. No. 7,419,487, filed Jul. 25, 2001, which claims priority to provisional application No. 60/220,639, filed Jul. 25, 2000. These related applications are incorporated herein in their entirety by express reference thereto.

FIELD OF THE INVENTION

This application relates generally to a method for performing tissue characterization using minimally invasive methods. More particularly, the application relates to a method and apparatus for performing an in vivo tissue characterization to identify and discriminate between diseased and healthy tissue using localized measurement of tissue impedance. Still more particularly, the application relates to method and apparatus for performing tissue characterization before, during and after ablative therapy using localized complex impedance measurement to monitor and titrate the delivery of ablative therapy to improve clinical outcomes.

BACKGROUND OF THE INVENTION

Various ablative therapies such as radio-frequency ablation, microwave ablation, and laser ablation can be used to treat benign and cancerous tumors. In theory, such methods are intended to produce physiological and structural changes to cause cell necrosis or destruction of the selected target tissue. However, in practice, there are numerous difficulties in the use of ablative procedures to treat cancerous tissue; these include: (i) locating the target tissue, (ii) identifying or biopsying the disease state of the tumorous tissue, (iii) distinguishing between diseased tissue versus healthy tissue, (iv) placing and maintaining the position of the ablation apparatus within the target tissue site, (v) monitoring the progress of ablation (including the developing ablation volume), (vi) minimizing injury to adjacent critical structures, (vii) assuring complete ablation of the tumor mass (including assurance of a sufficient healthy tissue margin), and (viii) assessing degree of the completed ablation. Current ablative therapies have not considered nor provided solutions to these problems. Thus, there is a need for treating cancerous tissue, which steps include (i) locating the target tissue, (ii) identifying or biopsying the disease state of the tumorous tissue (iii) distinguishing between diseased tissue versus healthy tissue, placing and maintaining the position of the ablation apparatus within the target tissue site, (iv) monitoring the progress of ablation including the developing ablation volume, (v) minimizing injury to adjacent critical structures, (vi) assuring complete ablation of the tumor mass including assurance of a sufficient healthy tissue margin and (vii) assessing degree of the completed ablation.

An embodiment of the invention provides an apparatus for detecting and treating tumors using localized impedance measurement. The apparatus comprises an elongated delivery device that includes a lumen and is maneuverable in tissue. An impedance sensor array is deployable from the elongated delivery device and configured to be coupled to at least one of an electromagnetic energy source or a switching device. The impedance array includes a plurality of resilient members, at least one of the plurality of resilient members being positionable in the elongated delivery device in a compacted state and deployable with curvature into tissue from the elongated delivery device in a deployed state. In the deployed state, the plurality of resilient members defines a sample volume. At least one of the plurality of resilient members includes an impedance sensor and at least a portion of the impedance array is configured to sample tissue impedance through a plurality of conductive pathways. An energy delivery device is coupled to one of the impedance array, the at least one resilient member or the elongated delivery device.

The apparatus can be configured to detect, locate and identify tumorous tissue at a selected tissue site using impedance measurements such as multi-pathway measured impedance, complex impedance and impedance vector measurements. For complex impedance real and imaginary components of the impedance signal can be used to determine more refined bioelectric parameters such as interstitial and intracellular impedance and cell membrane capacitance that provide greater sensitivity and predictive power of cell necrosis or malignancy. Also, the apparatus can be configured to utilize one or more impedance measurements to monitor a target tissue site and control the course of ablative therapy before during or after the delivery of ablative energy or other treatment to the tissue site. Accordingly the apparatus can be configured to be used independently or in conjunction with another ablative apparatus such as an RF, microwave or laser ablation apparatus. Further, the apparatus can be configured to utilize multi-path impedance measurement to monitor two or more tissue volumes including a tumor volume, a developing ablation volume and an adjacent anatomical structure. Additional embodiments of the apparatus can also be configured to utilize impedance measurements such as complex, vector or locus impedance measurements to generate an image of a target tissue site and display the image to facilitate the location and monitoring of a tumor and/or ablation volume.

In the use, the apparatus would be positioned at a selected tissue site previously imaged and found to contain a tumor or other tissue mass. The apparatus would be introduced and positioned at the tissue site using the elongated delivery device or an introducing device known in the art. The impedance array would then be deployed and used to measure impedance including complex impedance and capacitance through one or more conductive pathways. This information could be analyzed by coupled logic resources and then utilized to locate the position of and borders of the tumor volume and/or identify the tumor or tissue type. Also, the information could be processed by the logic resources or other processing means to generate an image of the tissue site including the tumor volume which could utilize the locus of impedance as a way to indicate the center of the tumor mass or otherwise visually enhance the detection and display of the tumor mass. This information could then be used to position the energy delivery device to produce the desired ablation volume. Once the energy delivery device was positioned, the impedance array could then be utilized to monitor and/or control the delivery of ablative energy or therapy to the tumor volume including monitoring the size and shape of a developing ablation volume in relation to size and location of the tumor volume. This allows the medical practitioner to not only determine the degree to which the tumor volume has been ablated, but also allows for the control of the amount of healthy tissue margin around the tumor volume one or all of which allow for the determination of a desired clinical endpoint. Further, it allows the practitioner to titrate or otherwise control the delivery of energy or other ablative therapy to control rate of growth of the ablation volume (and in turn the overall ablation time) as well as the final shape and size of the tumor volume. Multiple tissue volumes can be simultaneously monitored and compared to monitor progress of the ablation volume, assure uniform ablation or necrosis throughout the tumor or ablation volume and provide real time assurance that surrounding healthy tissues and structure were not injured. For example, tissue volume at the center, and one or more peripheries of the tumor mass could be simultaneously or near simultaneously monitored to assure uniform necrosis at all locations and hence throughout the tumor volume. Impedance measurements can be taken simultaneously or sequentially at multiple conductive pathways passing through the target volume (at convergent divergent and paths) to provide a higher confidence of uniform ablation by reducing the size of un-sampled zones within the target volume as well any directional bias of the measurements. The multiple conductive pathways can be selected electronically via a controllable switching device or manually by rotational, lateral or longitudinal movement of the impedance array within the target volume. In the former case, the user could program the conductive pathways via a coupled monitoring device and in the latter, the user could rotate, advance, retract or deflect the impedance array via the elongated delivery device or via a deployment, advancement or deflection device mechanically coupled to the impedance array or delivery device. In addition to real time impedance measurement during the ablation process, measurements can also be taken post ablation at one or more pathways, (including pathways different than those used during inter-ablative monitoring) and compared to baseline measurements or an impedance database to provide a further indication of a complete ablation and/or clinical endpoint. Endpoints can also be determined based on ratios of intracellular to interstitial impedance as well as a characteristic shape of the impedance or complex impedance curve including determinations of thresholds, slopes or inflection points.

Various aspects of the invention can also be directed to display impedance measurements in a variety of manners that are both user-friendly and easily discernible by the user/medical practitioner. In an embodiment, the loci of impedance of a sample volume or an impedance vector of the sample volume can be displayed as icons to facilitate tumor identification and positioning of an energy delivery or ablative device within the tumor mass. In related embodiments logic resource of the apparatus could be configured to use impedance vector measurements to determine the radial direction of the tumor from the impedance array or energy delivery device and display this information in the form of a directional or pointing icon.

SUMMARY

One method of treatment involves providing one or more radio-frequency energy delivery members configured for tissue insertion; inserting at least one of the delivery members into a tissue; forming a tract in the tissue by the delivery member; moving the delivery member along the formed tissue tract; and ablating the formed tissue tract with radio-frequency energy that is delivered by the delivery member. The tissue may include living malignant cells, while the ablated tissue tract is substantially free of living malignant cells. The delivery member may include one or more deployable delivery members therein. The delivery member may include one or more fixed or movable insulative members. The delivery member may be an introducer. The delivery member may include a conductive distal portion through which the ablative energy is delivered to the tissue tract.

One apparatus may include one or more radio-frequency energy delivery members configured for insertion into a tissue to form a tract therein, a radio-frequency power source coupled to at least one of the delivery members, and one or more logic resources coupled to the power source and to the at least one delivery member. At least one of the logic resources may include an algorithm or software configured for enabling the delivery of radio-frequency energy from the power source to the at least one delivery member for ablation of the tissue tract.

Another apparatus may include one or more delivery members configured for insertion into a tissue to form a tract therein. At least one of the delivery members may include one or more electrically conductive areas for the delivery of thermal ablative energy to the tissue tract, one or more outer impedance sensor, and one or more inner impedance sensing members positionable within the delivery member. At least one of the outer sensors and at least one of the inner sensing members may be configured for bipolar measurement of localized impedance of a tissue volume adjacent to the at least one inner sensing member. The at least one delivery member may be deployable. The at least one delivery member may include at least one insulative member disposed adjacent to a distal portion that includes at least one of the elect ally conductive areas.

A further apparatus may include one or more delivery members configured for insertion into a tissue to form a tract therein. At least one of the delivery members may include one or more electrically conductive areas for delivery of electroporation ablation therapy to the tissue. At least one of the conductive areas may be also for the delivery of thermal ablative energy to the tissue tract. The apparatus may include multiple electrically conductive areas disposed on different treatment delivery devices. The apparatus may include multiple electrically conductive areas disposed on different delivery members that are parallel to each other and electrically isolated from each other. The apparatus may include multiple electrically conductive areas disposed on one of the delivery members and electrically isolated from each other.

BRIEF DESCRIPTION OF FIGURES

FIG. 3B is a schematic view illustrating the use of primary and secondary conductive pathways and conductive pathway angle there between.

FIG. 4A illustrates an embodiment of the apparatus having a centrally positioned return electrode surrounded by other impedance sensing members.

FIG. 4B illustrates an embodiment of the apparatus having a centrally positioned return electrode surrounded by other impedance sensing members.

FIG. 4C illustrates an embodiment of the apparatus having the return electrode eccentrically positioned with respect to other impedance sensing members.

FIG. 4D illustrates an embodiment of the apparatus having multiple and independently positionable impedance sensor arrays.

FIGS. 15A-15H are lateral views of the electrodes, ring-like, ball, hemispherical, cylindrical, conical, needle-like, and a combination of a conical and needle-like.

FIGS. 26A-26G are plots of energy density or concentration versus lateral distance from the electrode/energy delivery device of the embodiments of FIGS. 25A-25C.

DETAILED DESCRIPTION

Figure 1:
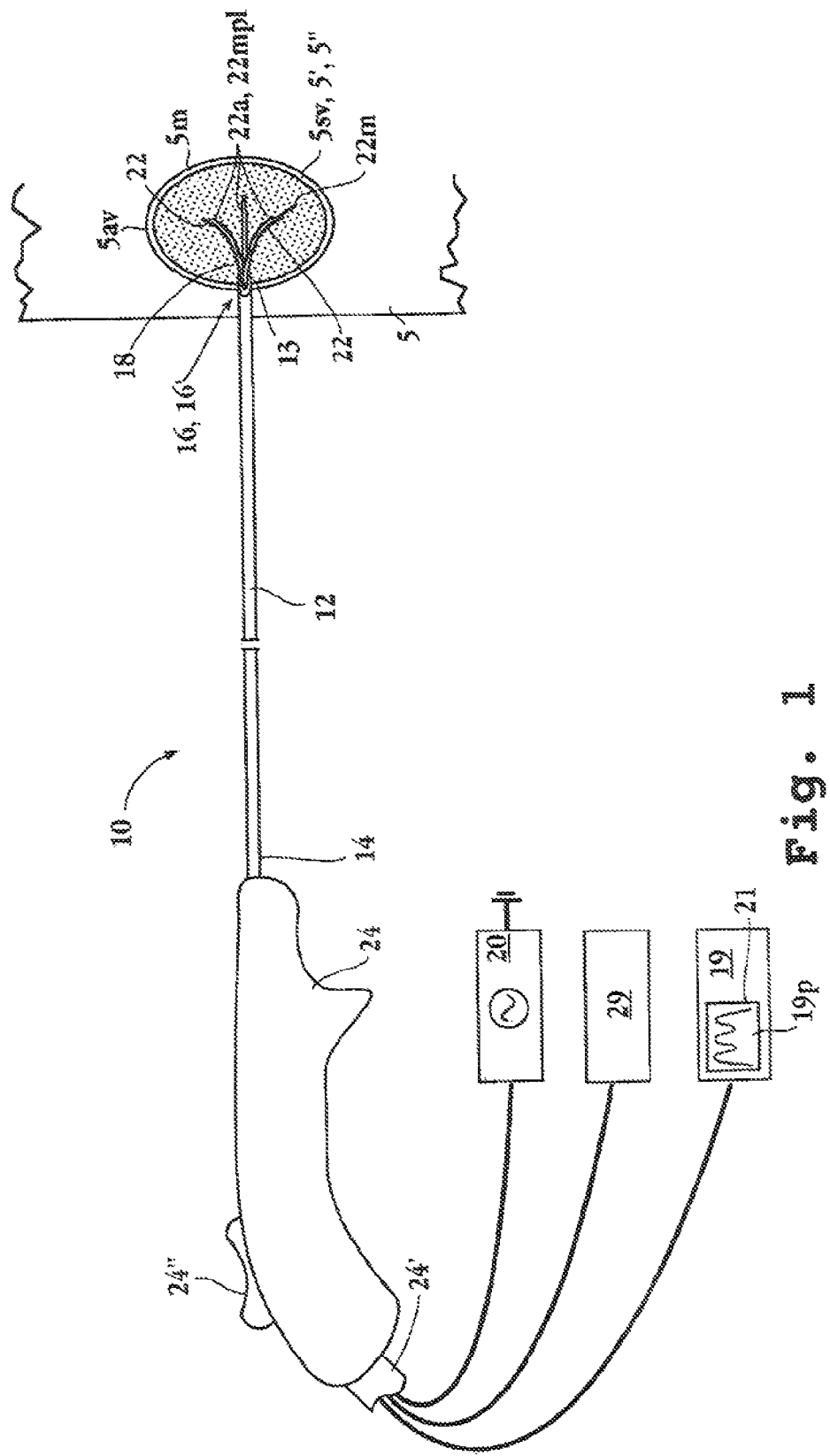
FIG. 1 is a lateral view illustrating the placement of a treatment apparatus at a tissue site.

Embodiments of the present application provide an apparatus and method for performing tissue characterization using localized impedance measurement including complex impedance measurement to locate and diagnose a tumor, accurately position an ablative apparatus, monitor the progress of an ablative treatment and determine clinical endpoints. Further, these and other embodiments can be configured to measure and analyze bioelectric parameters with enhanced predictive power of cell metabolism, along with associated images that allow for real time control of the ablative process, while significantly reducing the risk of incomplete ablation or unwanted damage to critical anatomical structures. Each of the disclosed embodiments may be considered individually or in combination with other variations and aspects of the application. The method and apparatus provided herein are useful in treating cancerous tumors in organs and tissue throughout the body, including, but not limited to, the liver, bone, breast, lung and brain. They are also useful and equally applicable for treatment of benign tumors, growths and otherwise abnormal or enlarged tissue that requires removal, resection or modification by surgical or minimally invasive means.

Localized monitoring of impedance is particularly beneficial for use in the treatment of tumors and tumorous tissue by ablative therapies, such as RF ablation, microwave ablation, laser ablation and chemical ablation. These and related ablative therapies cause disruption of cell membranes, resulting in impedance change in the interstitial fluid, but only in the affected tissue, with minimal or no changes to the surrounding tissue. Previous attempts to measure impedance using a full electrical circuit through the patient's body had the drawback of not being able to detect tissue localized impedance by failing to consider the problems involved, including the following: (i) the signal is too small in relation to, and/or masked out by, the impedance of the entire impedance measurement system (including the conductive pathway through body, the ground pad electrodes, and associated wires); (ii) the measurement is made too far away on the body from the desired tissue site, and is thus again masked out; and (iii) the localized impedance is masked out by RF or other ablative energy signal delivered to the tissue. Embodiments of the present application provide solutions to these problems by detecting localized impedance changes, particularly those changes occurring during an ablation procedure, through the use of impedance arrays positioned at the target tissue to measure impedance, including complex impedance and other bioelectric properties described herein.

A discussion will now be presented of impedance measurement theory and impedance measurement methods employed by embodiments of the application. In order to measure tissue impedance or impedivity (which typically has units of impedance/cc of tissue at 20° C.), a current is applied across the tissue and the resulting voltages are measured. This current, known as the excitation current or excitation signal, is relatively small in comparison to an ablative RF or other ablative current, and hence results in no appreciable ablative effect. In various embodiments, the excitation current can range from 0.01 mA to 100 amps, with specific embodiments of 0.1, 1.0 and 10 amps, which can be delivered in a continuous or pulsed fashion using a duty cycle. In various embodiments, the duty cycle can be in the range of 5 to 50%, with a pulse duration of 10 to 200 ms. The average power delivered over the course of the duty cycle can be in the range of 0.1 to 10 watts. In these and related embodiments, the excitation current source is used to measure voltage differences between two or more selected impedance sensors/sensing member in a bipolar mode or between one or more sensors/sensor members and a common ground in a monopolar mode. The known excitation current and the measured voltage are then used to derive impedance using algorithms and methods described herein and/or known in the art.

Because different frequencies are conducted differently through different tissue types, some tissue is more or less conductive at certain frequencies than others. Accordingly, depending upon the tissue type or condition to be detected, the sensing or excitation signal can be varied or otherwise controlled to improve one or more of the sensitivity, accuracy, precision and resolution of an impedance measurement. In various embodiments, the excitation signal can be a mono-frequency signal or a multi-frequency signal, and can be constant or variable. In an embodiment, improved signal resolution, and thus more precise tissue analysis and characterization, can be achieved by use of a multi-frequency excitation signal and/or an excitation signal varied across a broad range of frequencies. In various embodiments, this range of frequencies can be from about 1 Hz to about 1 MHz, with specific embodiments of 0.5 Hz, 1, 5, 10, 25, 50, 100, 250, 500 and 750 kHz. Since the bioelectric distinctions (e.g. phase angle, impedance) between cancerous and healthy tissue can be the greatest at low frequencies, such as 100 Hz, in exemplary embodiments, measurements can be taken over a plurality of excitation frequencies below 100 Hz, with specific embodiments of 3, 4, 10 and 20 Hz. Other embodiments can be combining measurements below 100 Hz with those between 100 Hz to 5 kHz.

Further embodiments of the application can be configured to measure impedance at different excitation frequencies (either concurrently or sequentially), to obtain more robust data and hence more refined clinical diagnostic information. Using these and other data and methods, a plot of impedance versus frequency can be generated for a sampled tissue volume and analyzed to determine tissue type and tissue conditions of the sampled volume, as is more fully described herein.

Complex impedance includes both real and imaginary components, which reflect the phase shift between voltage and current (e.g. the voltage can lead or lag current depending on the electrical properties of the tissue). Various embodiments of the application can be configured to record both the real and imaginary components of complex impedance. This provides the benefit of providing more comprehensive information on the tissue, allowing analysis with a greater degree of accuracy, precision and resolution. These components can be determined by passing an excitation current through the target tissue and measuring impedance and/or any phase shift between the current and voltage as the signal is conducted through the target tissue.

In related embodiments, real and imaginary components of impedance can be used to determine intracellular impedance, interstitial impedance and cell membrane capacitance. These three elements, alone or in combination, can be used to uniquely characterize and identify tissue type and condition with increased amounts of specificity. In an embodiment, the monitoring device, or other logic resources, can be configured to utilize one or more of these three parameters (the "three parameters") to characterize an amount of ablation or progression of tissue ablation from an ablative treatment, such as RF ablation or ablative methods described herein. The characterization can be done by a software module resident within the monitoring device, power supply, or coupled logic resources, all described herein.

In specific embodiments, the three parameters can be used to detect various physiologic indicators of ablation and cell necrosis, including cell lysis, cell membrane swelling (indicated by an increase in membrane capacitance), cell membrane rupture (indicated by a sharp decrease in membrane capacitance), a decrease in extracellular fluid (indicated by an increase in intracellular impedance), and an increase in intracellular fluid (indicated by a decrease in extracellular fluid). Other parameters which can be calculated and used for detection and control purposes include the absolute value of the impedance or admittance, the phase of the impedance (e.g. the phase difference between the current and the voltage), the capacitance, or a function of a combination of the impedance and admittance components.

Specific embodiments of the application can be configured to detect and/or control for threshold increases or decreases in one or more of the three parameters (or other variables), including increases or decreases in the ranges of 1.1:1.0 to 100:1.0, with specific embodiments of 1.5:1.0, 2:1, 3:1, 4:1, 5:1, 10:1, 20:1 and 50:10. Related embodiments can be configured to detect and/or control for combinations of increases or decreases in the parameters, including, but not limited to: a rise followed by a decrease in extracellular impedance, a decrease followed by an increase in intracellular impedance; and an increase followed by a decrease in cell membrane capacitance. Other related embodiments can be configured to detect, monitor and control for changes in the slopes of the curves of one or more of the three parameters. Still other related embodiments can employ PID control methods known in the art, utilizing combinations of proportional, integral or derivative changes in the three-parameter curves.

Embodiments of the application can incorporate the three parameters into electronic algorithms/software programs which are configured to do one or more of the following: (i) control the delivery of power to the target tissue site, (ii) provide the medical practitioner with prompts and diagnostic information about the course of the ablation/treatment process, and (iii) provide the medical practitioner with an indication of a clinical endpoint.

Referring now to the drawings, FIG. 1 shows an embodiment of an impedance monitoring and treatment apparatus 10 configured to detect and treat a tumor mass 5" in a target tissue site 5', by sampling the impedance 19$p$ of the tissue mass 5" and delivering energy or other ablative treatment to produce an ablation volume 5$av$. The apparatus 10 can be configured to measure impedance 19$p$, including complex impedance, before, during and after an ablation, so as to perform tissue identification at the target site 5', monitor the progress of an ablation procedure (including the developing ablation volume 5$av$), and quantitatively determine a clinical endpoint for the procedure.

Figure 2:
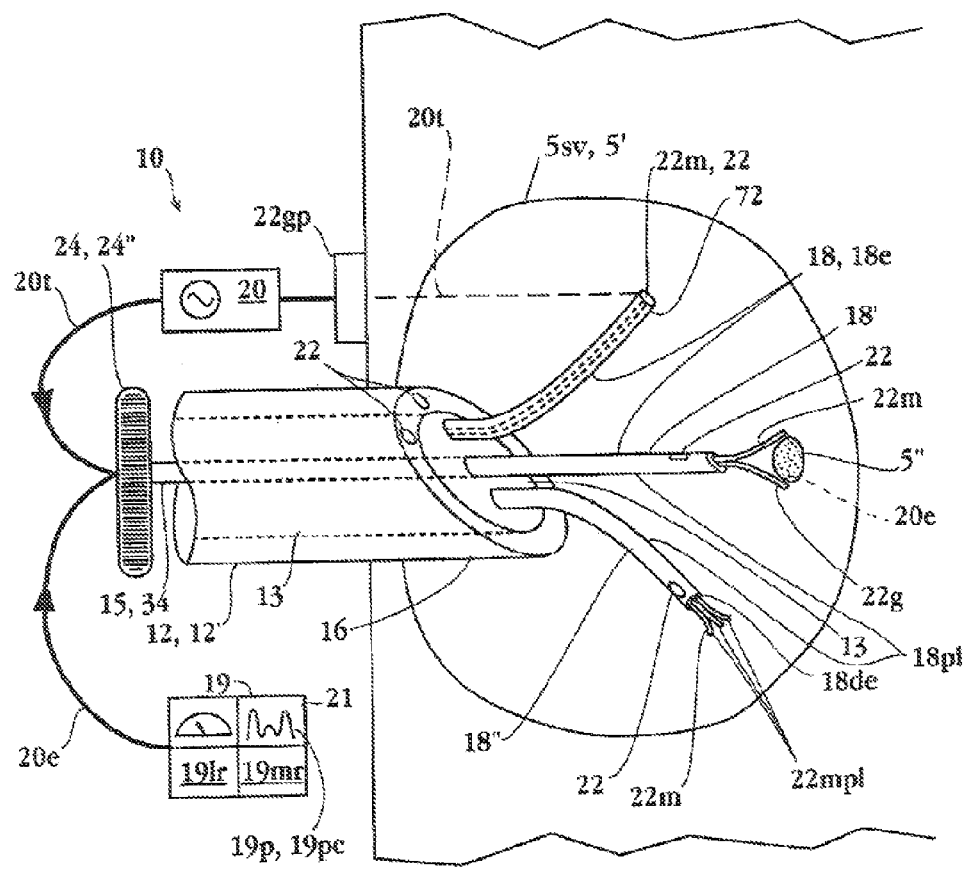
FIG. 2 is a lateral view of an apparatus including an elongated delivery device, impedance sensor array, sensors, resilient members, energy delivery device and advancement member.

Referring now to FIGS. 1 and 2, an embodiment of treatment apparatus 10 comprises an elongated member or introducer 12 having a lumen 13, a proximal portion 14, a distal end 16, one or more resilient members 18 positionable in lumen 13, and one or more impedance sensors 22 disposed on members 18, or impedance sensing members 22m positionable in lumens 72 disposed within members 18. Distal end 16 may be sufficiently sharp to penetrate tissue 5, including fibrous and/or encapsulated tumor masses, bone, cartilage and muscle. Lumen 13 may extend over all or a portion of the length of introducer 12. Members 18 can comprise a plurality of resilient members 18pl configured to be positionable in lumen 13, and advanceable in and out of distal end 16 by an advancement device 15 or advancement member 34, or other means described herein. Resilient members 18 can be deployed with curvature from introducer 12 to collectively define a volume 5av in target tissue site 5'. In an embodiment, all or a portion of one or more of members 18 can be an energy delivery device or energy delivery member 18e described herein. Energy delivery device 18 or member 18e can be coupled to an energy source or power supply 20 and can also include one or more lumens 72.

Embodiments of the application can be adapted, integrated, or otherwise applicable to a number of ablative therapies, including, but not limited to, radio-frequency (RF) ablation, cryo-ablation, brachytherapy, alcohol tissue ablation, chemical ablation, microwave ablation, laser ablation, thermal ablation, electroporation ablation, conformal beam radiation ablation, standard radiation ablation, high intensity focused ultrasound ablation, photo-dynamic therapy ablation. These and related embodiments can comprise an energy delivery device and sensing device coupled to a power supply.

For ease of discussion, the energy delivery device and sensing apparatus 10 will be an RF based apparatus and power supply 20 will be a RF power supply; however, all other embodiments discussed herein are equally applicable. In an embodiment, the RF power supply 20 can be an RF generator configured to deliver a treatment current 20t for tissue ablation, while simultaneously or near simultaneously (using a multiplexing/switching device) delivering a low power sensing or excitation signal 20e at one or more frequencies for making complex impedance measurements and subsequent analysis of the target tissue 5'. The excitation signal 20e can be delivered across a broad band of frequencies in the range of 1 to 1 MHz. In various embodiments, the excitation signal 20e is delivered at a lower frequency than the treatment signal 20t (typically 460±60 kHz). In an embodiment, the excitation signal 20e is less than 400 kHz. In other embodiments, the sensing signal 20e is in the range of 1 Hz to 100 kHz, with specific embodiments of 0.25, 0.5, 1, 5, 10, 25, 50 and 75 kHz. In alternative embodiments, the excitation signal 20e is delivered at frequencies above the treatment frequency and thus can be greater than 520 kHz. Further, the frequency and power differences between the excitation and treatment signals 20e and 20t can be monitored and set-point controlled using circuitry and control algorithms known in the art. Also, the frequency and power difference between the two signals 20e and 20t can be varied responsive to one or more electrical parameters, to maximize the accuracy and precision of impedance measurements 19p and reduce interference (e.g. bleed over) from the treatment signal 20t. These electrical parameters include, but are not limited to, impedance, treatment current, treatment frequency, excitation current and excitation frequency.

In various embodiments, introducer 12 can be flexible, articulated and steerable, and can contain fiber optics (both illumination and imaging fibers), fluid and gas paths, and sensor and electronic cabling. In an embodiment, introducer 12 can be configured to both pierce tissue 5 and be maneuverable within tissue 5. This can be achieved through the use of flexible portions coupled to a tissue piercing distal end 16 that can be a needle or tracer tip integral or joined to introducer 12. Introducer 12 can be sufficiently flexible to move in any desired direction through tissue 5 to a desired tissue site 5'. In related embodiments, introducer 12 is sufficiently flexible to reverse its direction of travel and move in a direction back upon itself. This can be achieved through the use of flexible materials and/or deflecting mechanisms described herein. Also, introducer 12 can be coupled at its proximal end 14 to a handle or handpiece 24. Handpiece 24 can be detachable and can include ports 24' and actuators 24".

One or more impedance sensors 22 can be coupled to introducer 12, resilient members 18, or energy delivery device 18e. In an embodiment, sensors 22 can comprise one or more sensing members 22m that can be positionable within lumens 72 of members 18, and configured to be advanceable in and out of individual members 18, or can be coupled to an exterior of resilient member 18. Sensing members 22m can comprise a plurality of members 22mpl positioned in multiple resilient members 18. Also, apparatus 10 can have impedance sensors 22 disposed along elongated member 12 and other locations outside of the target tissue site 5' for measurement and determination of the total impedance across the full electrical circuit between the terminals of power supply 20 (i.e. through the patient's body and to the ground pad). The total impedance can be monitored and otherwise utilized to improve the accuracy and precision of the localized impedance measurement from the target site 5'.

Figure 3A:
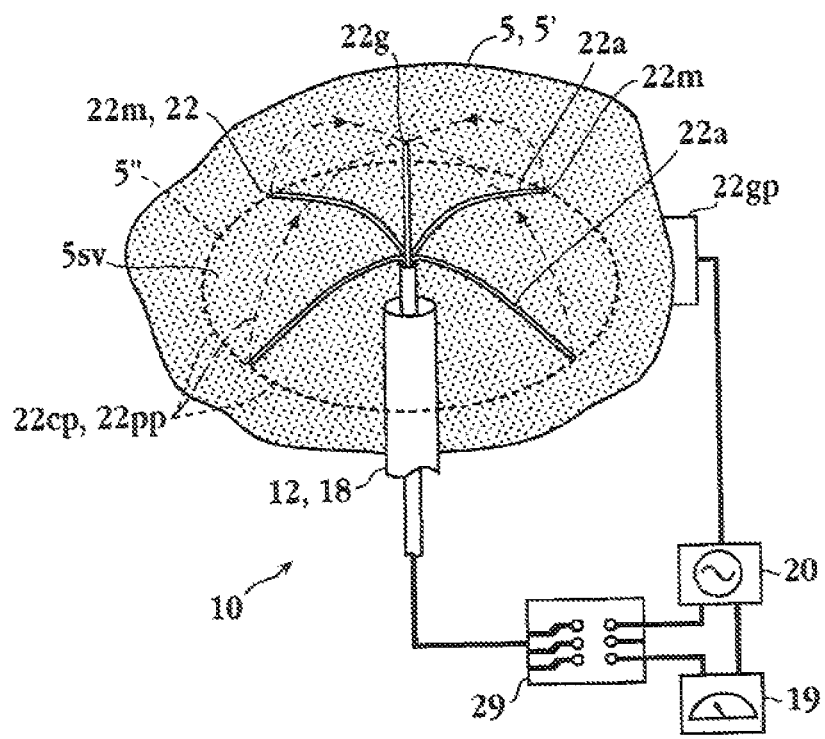
FIG. 3A is a schematic view of an impedance sensor array configured to measure impedance of a tissue volume via a plurality of selectable conductive pathways.
Figure 3B:
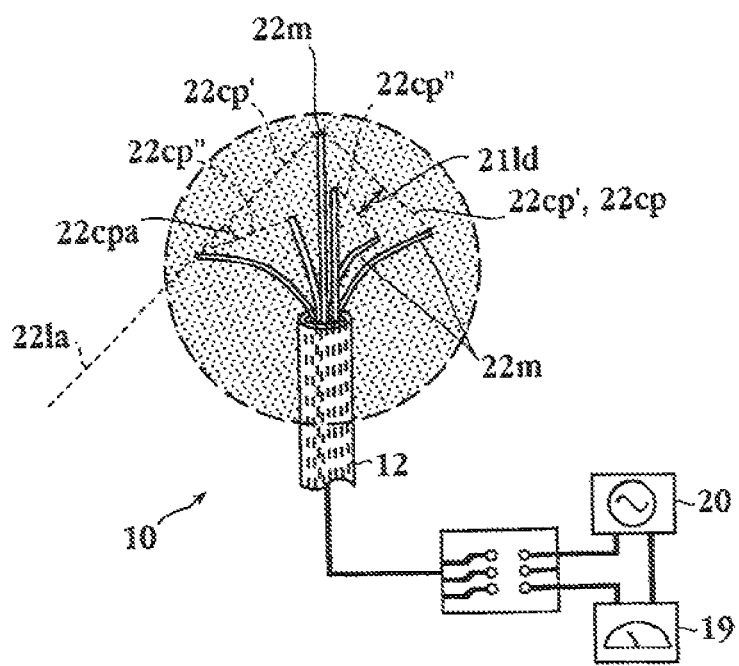

Impedance sensing members 22m, or sensors 22, coupled to resilient members 18 can be deployed independently or simultaneously to enable probing of target tissue 5' in multiple locations, so as to measure impedance 19p in multiple locations and/or through multiple conductive pathways 22cp (FIGS. 3A-3B). Deployment of impedance sensing members 22m or sensors 22 can be controlled such that telemetry can be used with impedance feedback to identify tissue types and map the topography of tissue masses, tumors or tissue structures.

Impedance sensing members 22m can also be deployed with curvature from members 18 to collectively define a volume 5sv (also called sample volume 5sv) that is volumetrically sampled by sensing member plurality 22mpl. Collectively, the plurality 22mpl of deployed impedance sensing members 22m, or the plurality 18pl of deployed resilient members 18 with coupled impedance sensors 22, can comprise a three-dimensional or volumetric impedance sensor array 22a. By having sensors 22 in multiple locations and planes, sensor array 22a is configured to volumetrically sample (e.g. sample in multiple locations and through multiple conductive pathways) tissue within target tissue site including tumor mass 5". Sensor array 22a is further configured to be able to simultaneously sample tissue at multiple locations within volume 5sv or tissue site 5', to perform one or more of the following: (i) locate the position of the tumor mass 5", (ii) discern the position or deployment distance of the energy delivery members 18, (iii) monitor the developing ablation volume 5av, (iv) perform tissue sensing identification by comparing impedances 19p between two or more sites (e.g. known healthy tissue and suspected diseased tissue 5"). In various embodiments sensor array 22a and/or member plurality 18pl can be configured to define a variety of shapes for sample volumes 5sv, including, but not limited to, a hemisphere, a sphere, an oval, a cone, a pyramid, a polyhedron or a tetrahedron.

Each resilient member 18 can have one or more impedance sensing members 22m and/or sensors 22 that can be arranged in a variety of configurations to perform one or more of the desired functions described herein (e.g. tissue identification, ablative monitoring, etc.). Referring now to FIG. 3A, sensing members 22m can be configured to measure impedance in either bipolar mode (between two or more members 22m) or monopolar mode (between one or more selected members 22m and a common ground, such as a ground electrode 22g or ground pad electrode 22gp). Switching between the two modes can be controlled by logic resources and/or a switching or multiplexing device 29 coupled to, or integral with, an impedance monitoring device 19 or power supply 20. Further, switching device 29 can be configured to allow the user to define and select one or more conductive pathways 22cp to measure impedance. In use, these and related embodiments allow the user to select any number of conductive pathways 22cp and in a pattern 22pp that circumscribe or otherwise defines a sample volume 5sv of interest. Also, the use of switching device 29 in these embodiments allows the user to measure impedance simultaneously or sequentially through the selected pathways 22cp. Further, switching device 29 and/or apparatus 10 can be so configured to allow the user to dynamically change or switch between pathways 22cp, to do one or more of the following: (i) change the number of pathways 22cp through a selected sample volume 5sv, allowing increased signal resolution and statistical confidence of predicted tissue conditions; (ii) change the angle between two or more conductive pathways 22cp; (iii) change the size of the sample volume 5sv; (iv) switch between a first and second sample volumes 5sv; and (v) compare two or more sample volumes 5sv simultaneously.

In an embodiment shown in FIG. 3B, conductive pathways 22cp can include a primary pathway(s) 22cp' and an alternative pathway(s) 22cp". The alternative pathway 22cp" can be at a selectable angle 22cpa from the primary pathway 22cp', and can share points in common with the primary pathway 22cp'. Suitable angles 22cpa include the range of 1° to 360°, with particular embodiments of 30°, 45°, 90° and 270°, from a lateral axis 22la of the primary pathway 22cp". Alternatively, the alternative conductive pathway 22cp" can share one or more points in common with the primary pathway 22cp', or be parallel with the primary pathway 22cp' but offset a selectable lateral distance 22ld. Also, repetitive scans of impedance, including sweep scans and sequential sweep scans (e.g. sequentially sampling from one side of a sample volume 5sv to the other, similar to radar), can be made through one or more selected conductive pathways 22cp of a selected sample volume 5sv to monitor the time course of ablation, as well as to obtain improved signal to noise ratios and signal resolution for image analysis.

Changing the angle 22cpa and/or lateral offset 22ld of the conductive pathways 22cp used to measure impedance can be accomplished through a variety of means, including, but not limited to: (i) selectively switching impedance sensors 22 or sensing elements 22m off and on; (ii) selectively switching sensing elements 22m from a monopolar mode to a bipolar mode, and visa versa (for RF embodiments), using switching device 29; (iii) configuring the probe array 22a (FIG. 3A) to be rotatable and/or deflectable; and (iv) using and/or deploying a second array 22a either on the some device 10 or on a different device. Switching can be accomplished through the use of a switching or multiplexing device 29, which can be programmable or controlled by logic resources 19lr (FIG. 2) described herein.

In one embodiment, the data from alternative conductive pathways 22cp" or group of pathways 22cp can be integrated with measurements from the primary conductive pathways 22cp' for analysis and imaging purpose or, in an alternative embodiment, can be analyzed and displayed separately, allowing for a comparison of both measurements and images from the primary and alternative groups of pathways 22cp. The benefit of the former is a more representative and uniform sampling of impedance, and the later the ability to detect for uniformities of impedance within the sampled volume 5sv.

In use, such embodiments allow the medical practitioner to sample or image a larger tissue volume 5sv than single pathway sampling, and to sample multiple tissue volumes 5sv, including simultaneous sampling, without having to reposition the apparatus 10 or impedance array 22a (FIG. 3A). This capability reduces procedure time, and generally enhances the usability of the apparatus 10. Further, such embodiments also provide a more accurate and representative signal of the target tissue volume 5sv by selecting conductive pathways 22cp to control the shape and size of the sample volume 5sv, to sample only the area of interest, thereby eliminating any potential masking or undesired impedance contribution from surrounding non-target tissue 5. Also, the ability to switch the angle 22cpa of the pathways 22cp eliminates or reduces any directional bias in the impedance measurements. Finally, by virtue of having a larger and volume distributed sample size for a given volume of tissue 5sv, the use of multiple conductive pathway impedance measurements provides a more representative measurement of impedance for the selected volume 5sv, thereby improving the accuracy and precision of the impedance measurement as well as improving signal and image resolution in one or all three dimensions.

Referring now to FIGS. 4A-4D, in various embodiments, impedance sensing members 22m can be arranged in arrays (22a1, 22a2) having a variety of geometric arrangements and relationships, so as to electrically sample different volumes 5sv of tissue using different conductive pathways 22cp. Such embodiments provide the benefit of improved acquisition, accuracy and analysis of the impedance signal from a given sample volume 5sv to compensate for signal hysteresis, noise (due to energy delivery etc.), directional bias, or other error. They also provide the benefit of simultaneous sampling and comparison of two or more tissue volumes 5sv to perform tissue identifications.

Conductive pathways 22cp can have a variety of configurations and orientations, all selectable by the user. In an embodiment, the conductive pathways 22cp can be evenly distributed or spaced within the sample volume 5sv. This can be achieved by either the configuration of the members 22m, through the use of switching device 29, or a combination of both. Alternatively, the conductive pathways 22cp can be aligned with respect to one or more sensing members 22m, the introducer 12, or the tumor volume 5" itself. In an embodiment, shown in FIGS. 4A-4B, one member 22mc can be positioned at the center of sample volume 5sv, with other members 22m positioned in a surrounding relationship, so excitation current travels in a plurality 22pp of conductive pathways 22cp to and from the center of the sample volume 5sv to the surrounding impedance sensing members 22m. In use, this configuration results in an impedance measurement for the sample volume 5sv, which is an average of the individual impedance measurements for each conductive pathway 22cp, providing the benefit of a more a statistically representative sample of impedance for a selected tissue volume 5sv than provided by a single pathway sampling alone. Surrounding members 22m can be collectively coupled to a positive terminal of power supply 20, with member 22mc configured as a return electrode and coupled to a return terminal of power supply 20.

In a related embodiment, shown in FIG. 4C, member 22mc can be eccentrically positioned with respect to members 22m and/or positioned on the periphery of a sample volume 5sv defined by members 22m. Again, this embodiment provides the benefit of an average, and thus more representative, impedance measurement for the sample volume 5sv. However, this configuration also provides the benefit of being able to more readily detect and locate non-uniformities 5nu (in impedance and hence tissue properties) occurring on the boundaries or otherwise non-centered portions of the tissue volume 5sv. Use of switching device 29 allows for the dynamic switching of any of the sensing members 22m to a return electrode 22mc to more readily detect the location of a potential non-uniformity within the sample volume 5sv, by rapidly scanning different portions of the periphery of the volume 5sv.

Alternatively, as shown FIG. 4D, members 22m can comprise a first array 22a1 (such as perpendicular array) and a second array 22a2. First array 22a1 can be rotated to obtain different conductive pathways to second array 22a2 so as to sample different tissue volumes and/or provide multiple samplings of the same volume (via different conductive pathways), to improve accuracy and precision of the measurement, and reduce noise. In use, this embodiment also allows detection of incomplete ablation by comparing a measured impedance from a first group of conductive pathways 22cp1 defined by first array 22a1 to a second group of conductive pathways 22cp2 defined by second array 22a2.

Figure 5:
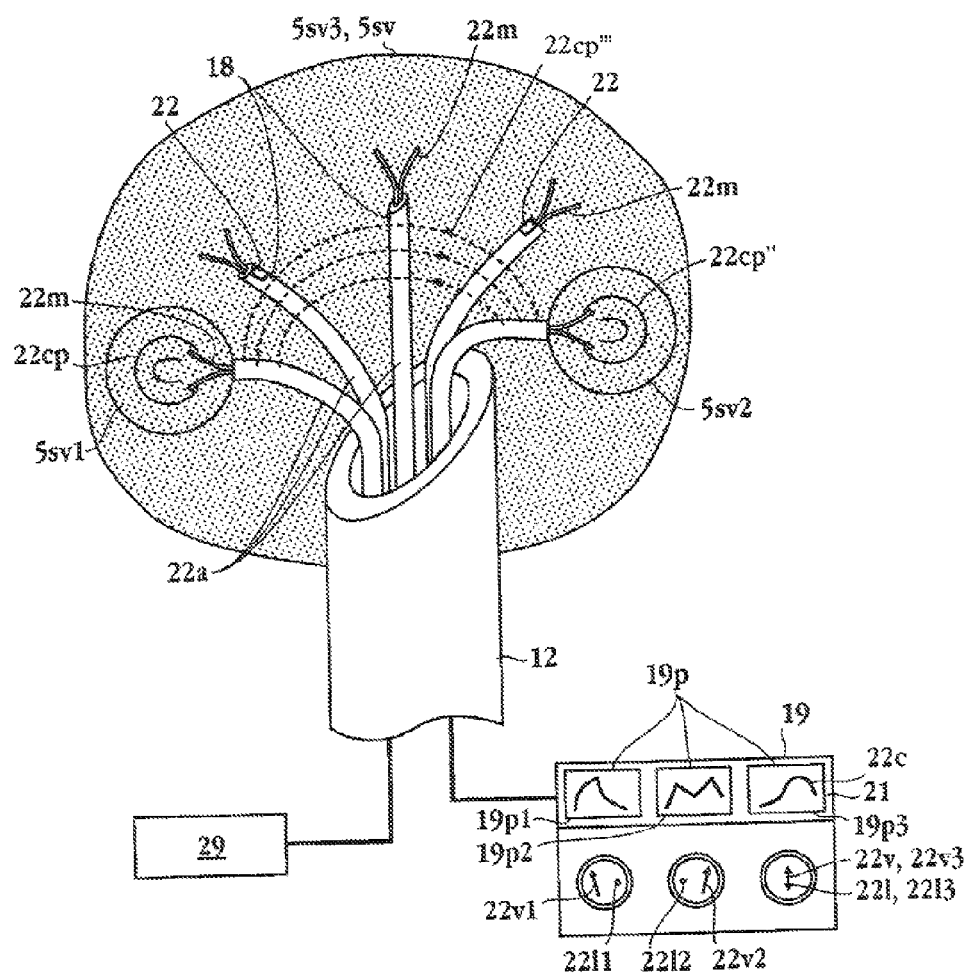
FIG. 5 is a perspective view illustrating the use of multiple groups of conductive pathways to sample multiple tissue volumes as well as to determine impedance vectors and loci of impedance for each sampled volume.

In various embodiments, apparatus 10 can be configured to simultaneously sample different locations within target tissue site 5' utilizing switching device or multiplexer 29, or other switching means described herein or known in the art. In an embodiment, shown in FIG. 5, a first group of selected conductive pathways 22cp' can be used to sample a local first volume 5sv1, and a second group of selected conductive pathways 22cp" can be selected to do so for a second volume 5sv2, and a third group of selected conductive pathways 22cp'" can be selected to do so for a larger or global sample volume 5sv3 that is defined or circumscribed by multiple sensor 22 tipped members 18 or sensing members 22m. Each sample volume results in a separate impedance profile 19p. Thus, sample volumes 5sv1, 5sv2, and 5sv3 produce impedance profiles 19p1, 19p2, and 19p3, respectively, all or portion of which can be compared to one another or a database of impedance profiles 19db, using comparison/pattern recognition algorithms of module 19m, or other software or computational means. In a related embodiment, the measured impedance signal for each sample volume can be integrated or otherwise analyzed by module 19m, or other computational means, to determine an impedance vector 22v and locus 22l of impedance for each respective sample volume (e.g. impedance vectors 22v1, 22v2, and 22v3, impedance loci 22l1, 22l2, and 22l3).

Figure 6:
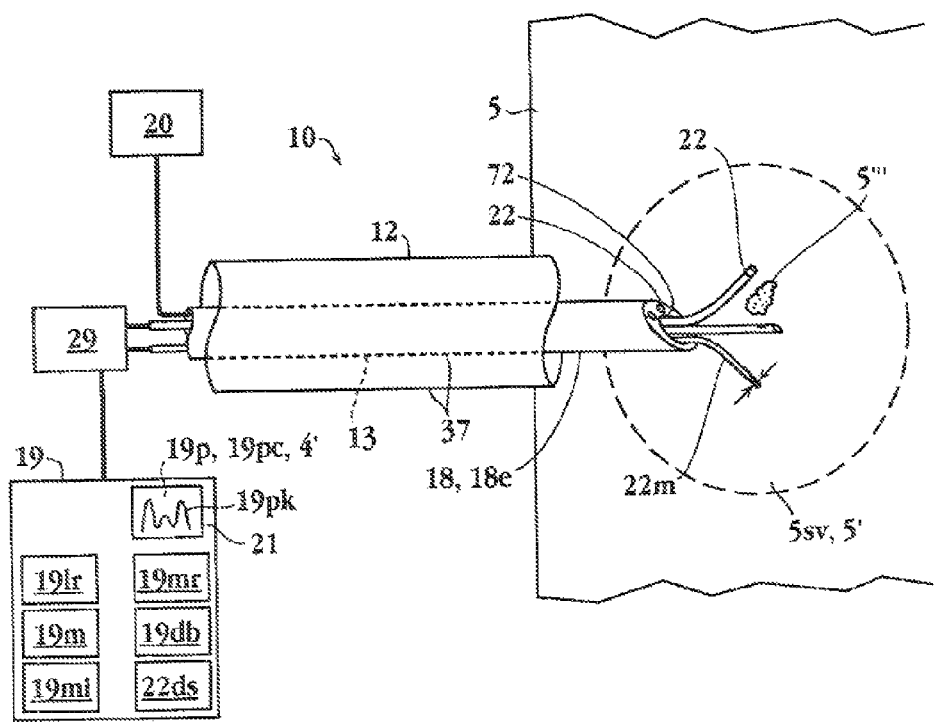
FIG. 6 is a perspective view of an apparatus including an impedance monitoring device having memory resources and logic resources (including software modules) to analyze impedance data and generate impedance profiles and images.

Referring now to FIG. 6, in an embodiment, one or more impedance sensors 22 or sensing members 22m of apparatus 10 can be coupled to an impedance measurement and monitoring device 19. Monitoring device 19 includes circuitry described herein to measure voltage from the excitation current and subsequently calculate impedance. Further, monitoring device 19 can also be configured to measure, calculate and record an impedance profile 19p and a complex impedance profile 19pc resulting from various tissue bioelectric properties, including impedance, conductance, capacitance, etc. In an embodiment, monitoring device 19 can include logic resources 19lr, such as a microprocessor and memory resources 19mr (such as RAM or DRAM chip) configured to analyze, store and display tissue impedance profile 19p and/or other bio-electric information derived from sensing member 22m and/or sensing array 22a. Impedance monitoring device 19 can also be coupled to a display device 21 so as to display real time or stored impedance profiles 19p, images, and other data generated by impedance monitoring device 19. Examples of display devices 21 include cathode ray tubes (CRTs), liquid crystal displays, plasma displays, flat panel displays, and the like. Display device 21 can also be incorporated in an external computer coupled to impedance monitoring device 19.

In various embodiments, impedance monitoring device 19 or power supply 20 can be equipped with a number of features, including but not limited to the following: (i) memory resources 19mr containing a database 19db of characteristic impedance profiles; (ii) a readout window for the impedance-based diagnosis of tissue type and/or condition; (iii) artificial intelligence algorithms/programming enabling the generator to learn from newly acquired impedance scans; (iv) ability for the user to enter and teach the generator the correct tissue type and condition, based on biopsy or pathology data; (v) ability to sense impedance on multiple frequencies simultaneously to improve speed and accuracy, and to reduce effects of interference; (vi) ability to work with non-invasive pads (like electro-physiology pads) for measurement of complex impedance, and for performing targeted tissue assessment non-invasively; (vii) ability to monitor a reference signal and/or basic patient electro-physiological conditions, for baseline comparisons with impedance readings and as additional information for the user; and (viii) programming to utilize the reference signal or signal to account for hysteresis, signal noise, cross talk and other signal interference, using digital subtraction, suppression and other signal processing methods known in the art, and thus improving a signal to noise ratio, signal sensitivity or resolution.

In various embodiments, apparatus 10, along with impedance monitoring device 19, can be configured to perform tissue identification, differentiation, ablation monitoring, and mapping of tissue masses and structures. In specific embodiments, monitoring device 19 is configured to perform a tissue identification function, using impedance information derived from sensors 22, sensing members 22m, or array 22a. A discussion will now be presented on the background of tissue monitoring and identification using impedance measurement. Owing to variations in composition and morphology, various tissue types have different electrical properties (e.g. conductance, inductance, capacitance, etc.), and therefore conduct electrical energy differently, particularly at certain frequencies. For example cancerous tissue will typically have a significantly higher phase than the health tissue, particularly at low frequencies. These differences in electrical properties, particularly in conductance, result in a characteristic impedance profile 19p for a given tissue type or condition when the tissue is exposed to an excitation current at one or more specific frequencies. Impedance profile 19p, which can have one or more peaks 19pk, curves 19pc, and other shapes that serve as a fingerprint of the tissue type or tissue condition. Accordingly, by analyzing the impedance profile 19p and matching peaks 19pk, curve shapes 19pc, thresholds, etc., profile 19p can be utilized by embodiments of the application to identify tissue types and conditions, such as malignancy, vascularity, necrosis, thermal injury, etc. Related conditions that can also be identified using this approach include abnormally mutated tissue, abnormally dividing tissue, or hypoxic tissue.

Further, many tissue types, including cancerous tissues such as metastatic tissue, will have a signature profile 19p that can be readily identified and matched to a database of profiles 19db, using pattern recognition techniques or algorithms known in the art. Accordingly, apparatus 10 can include electronic algorithms or software modules 19m resident in logic resources 19lr of monitoring device 19 or microprocessor 350 (FIG. 29) that are configured to analyze an impedance profile 19p (including real and imaginary components), and perform tissue identification and/or tissue differentiation between one or more sampled volumes 5sv. Modules 19m can include pattern recognition algorithms, curve fitting, fuzzy logic, or other numerical methods known in the art. Also in an embodiment, modules 19m can be configured to compare profile 19p to a database of profiles 19db stored in memory resources 19mr, and use curve fitting or other numerical methods known in the art to provide and display a correlation coefficient or statistic (e.g. p value) indicative of the probability of a match to a given tissue type or condition. Module 19m can also include an imaging sub-module 19mi, described herein, to generate and display an impedance image 4'.

In various embodiments, the impedance and other bioelectric properties that can be analyzed to determine a tissue type or condition include: complex impedance (real and imaginary components), extracellular impedance, intracellular impedance, interstitial impedance, cell membrane capacitance, and intracellular capacitance. In an embodiment, monitoring device 19 can be configured to analyze only selected frequencies of an impedance profile 19p or other bioelectric property measurement that are known to identify, or correlate to, selected tissue characteristics, rather than analyzing the full frequency spectrum of the profile 19p. Such frequencies can be selected from a pre-existing database 19db, or determined in vivo using swept frequency methods described herein. This approach presents the advantage of shorter signal processing times, allowing a faster tissue assessment and diagnosis using fewer computational resources. In turn, this enables the size, power requirements, and complexity of the control and display instrumentation 19 to be reduced.

Figure 7A:
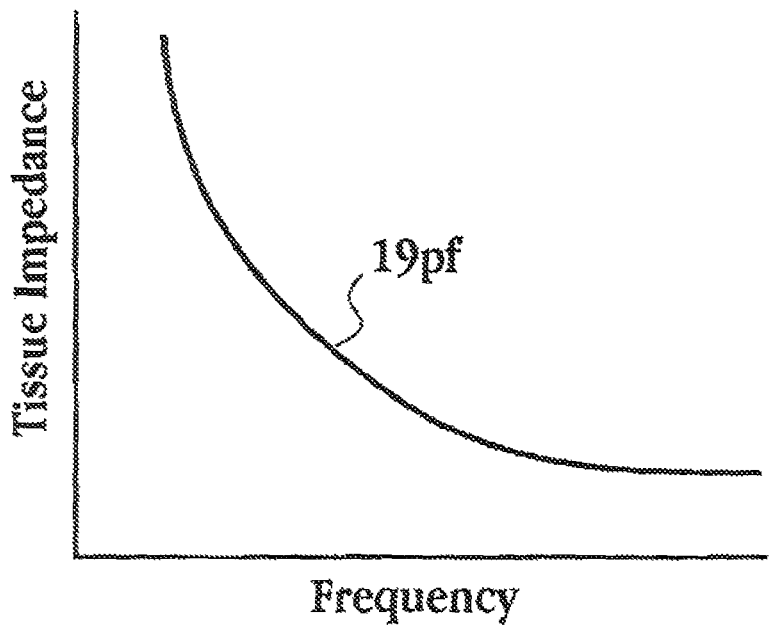
FIG. 7A is a plot of tissue impedance curve illustrating the frequency dependency of impedance.
Figure 7B:
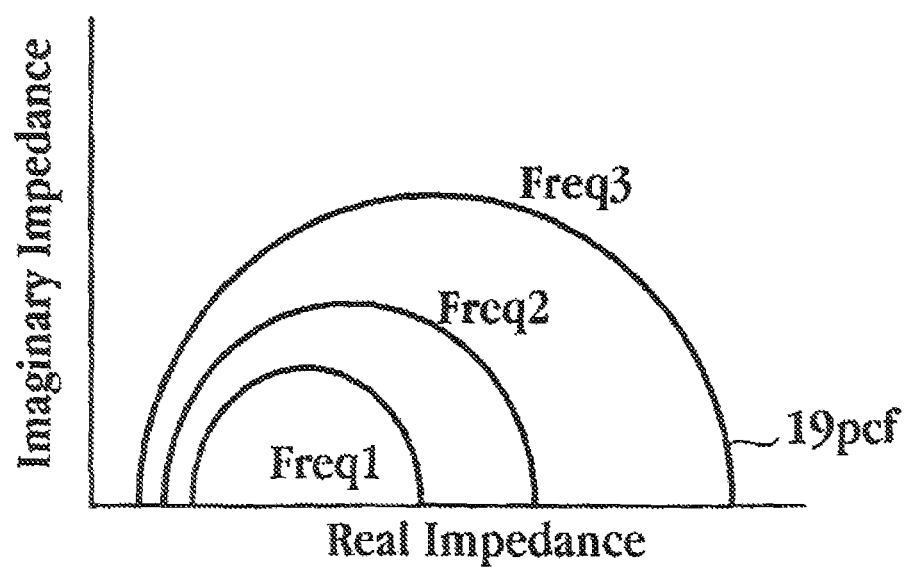
FIG. 7B is a plot of tissue complex impedance curves illustrating the frequency dependency of complex impedance.

Referring now to FIGS. 7A-10, in related embodiments, apparatus 10 and monitoring device 19 can be configured to utilize complex impedance curves to identify and characterize different tissue types and conditions. Accordingly, monitoring device 19 can be configured to measure, generate, and display curves of profiles 19pc of complex impedance. Curves 19pc can be both two-dimensional and three-dimensional. For two-dimensional plots, the x-axis can be the real component and the y-axis the imaginary component (FIG. 7B); while three-dimensional plots can include an axis for time or frequency. This can be accomplished via algorithms within modules 19m or 19mi that receive input from impedance array 22a, perform complex impedance calculations known in the art and curve fitting or transform functions described herein, and subsequently output an impedance profile 19p that is displayed on display device 21 (FIG. 6). As shown in FIGS. 7A and 7B, because tissue conducts electrical current differently at different frequencies, measurements made across a range of excitation frequencies results in an impedance frequency response curve 19pf (FIG. 7A), or a series of complex impedance frequency response curves 19pcf (FIG. 7B). Using either of the frequency response curves from FIGS. 7A or 7B, a particular frequency can be selected for subsequent impedance complex impedance measurements and analysis which has the greatest sensitivity for a given tissue type or condition and/or results in a complex impedance curve having the greatest predictive value for the desired tissue type or condition. The selection can be done using methods described herein, or by calibration against a set of in vitro standards representative of the desired tissue type or condition, by visual determination/estimation of the user, or a combination thereof.

Figure 8A:
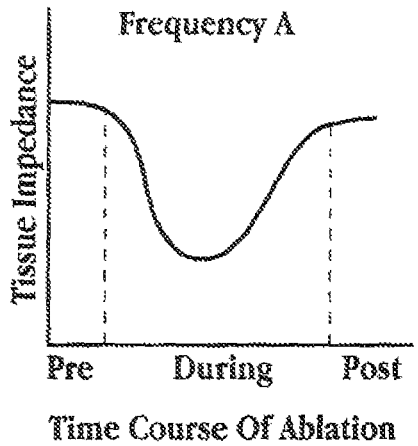
FIGS. 8A-8D are plots of impedance curves illustrating the use of multiple frequency impedance curves to monitor the time course of an ablation.
Figure 8B:
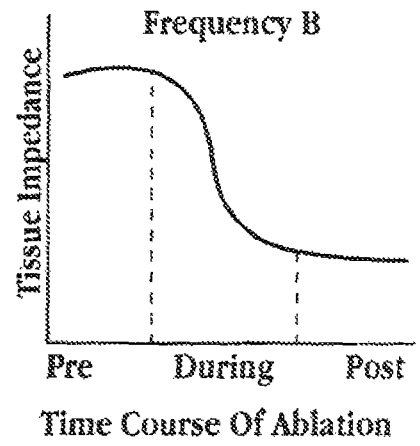
Figure 8C:
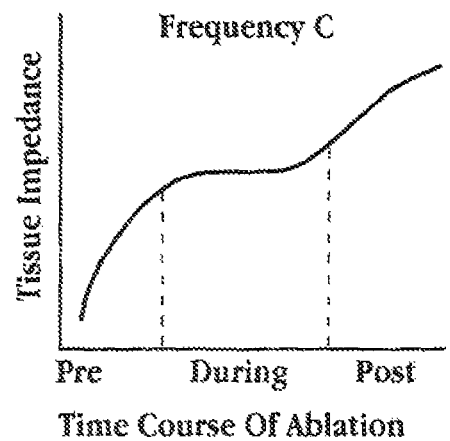
Figure 8D:
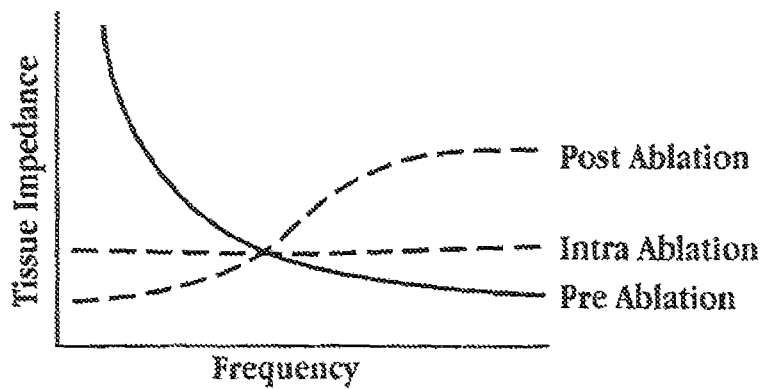

As shown in FIGS. 8A-8C, in an embodiment, the course of an ablation can be monitored using impedance measurements made at multiple frequencies. The impedance at some frequencies will rise, fall or do both over the time course of the ablation. By combining impedance data from multiple curves, the overall predictive value of the measurements for an ablation event or endpoint is greatly increased. Accordingly, using differential diagnosis methodology, an ablation monitoring algorithm or module 19m can be configured to look for impedance characteristic curve shapes, slopes threshold, etc., in two or more impedance curves made at different frequencies as predictors of an ablation endpoint. Such information can be used to provide a more reliable indicator of clinical endpoint, as well as to monitor and titrate the delivery of ablative energy or ablative therapy according to the requirements. Similarly, as shown in FIG. 8d, differences in the impedance-frequency spectrum pre-, inter-, and post-ablation can also be used to monitor and evaluate the ablation process.

Figure 8E:
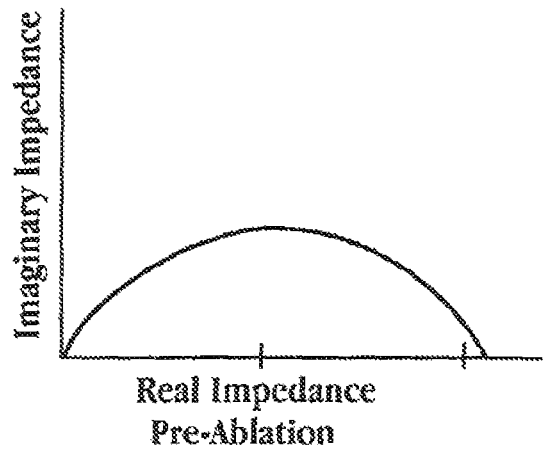
FIGS. 8E-8G are plots of complex impedance curves (imaginary vs. real values) illustrating the use of complex impedance curves to monitor the time course of an ablation.
Figure 8F:
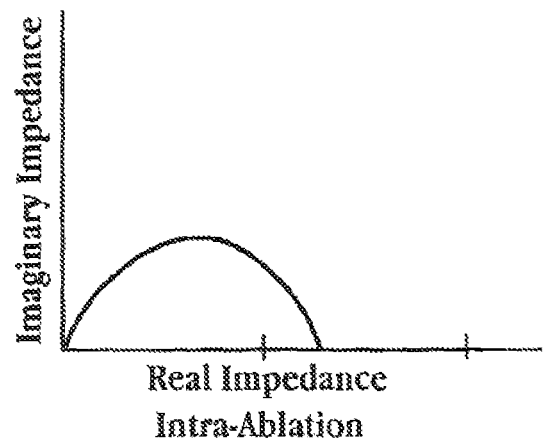
Figure 8G:
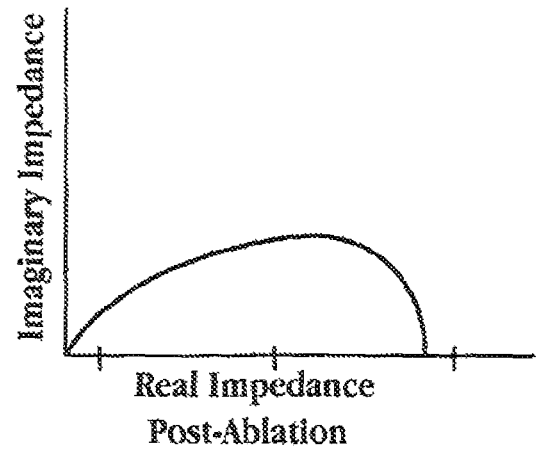
Figure 9A:
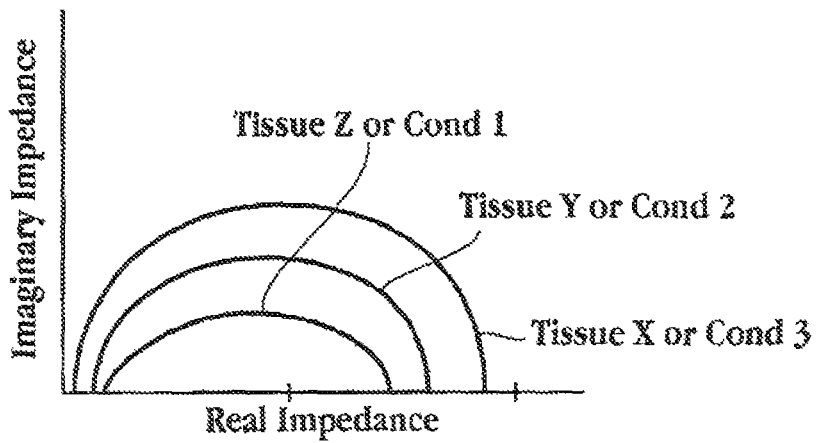
FIGS. 9A-9C are plots of complex impedance curves illustrating the use of complex impedance curves to identify tissue type or condition.
Figure 9B:
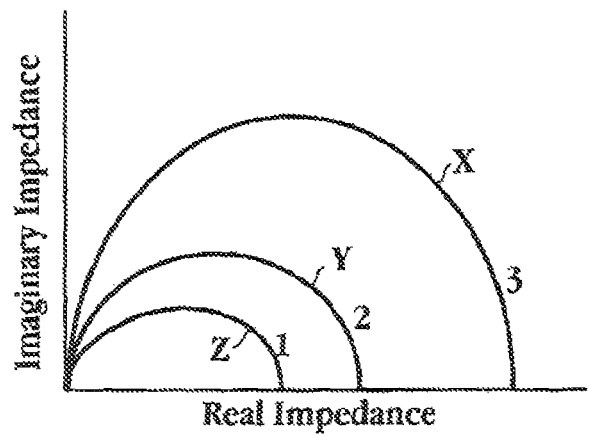
Figure 9C:
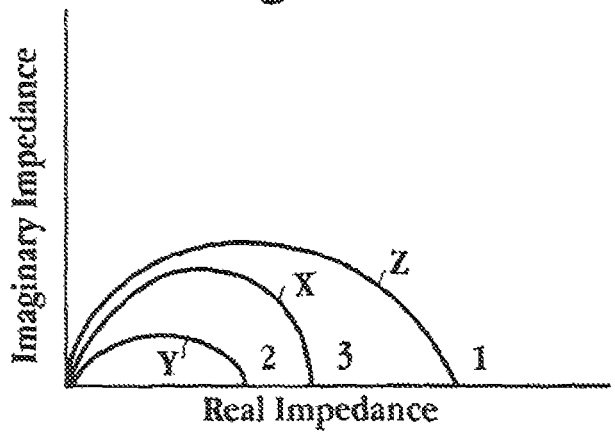
Figure 10:
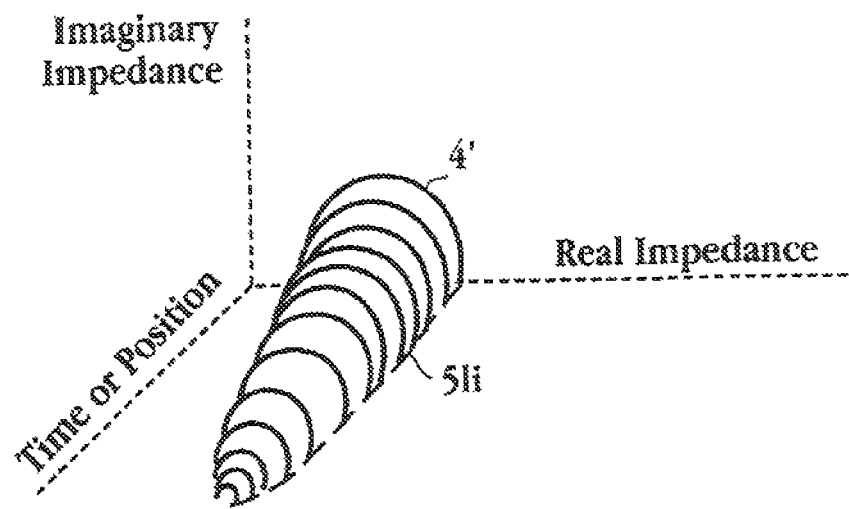
FIG. 10 is a three-dimensional plot of complex impedance.

In related embodiments, shown in FIGS. 8E-8G, complex impedance curves 19pc can be used to monitor and assess the ablation process, including determination of clinical endpoints, as described herein. Further, as shown in FIGS. 9A-9C, the apparatus can be configured to utilize complex impedance curves to identify and characterize different tissue types (tumors, etc.). Related embodiments can be configured to generate and display three-dimensional plots of complex impedance utilizing time and or position as the third axis. For positional 3-D plots, the locus of impedance 5li can be calculated and graphically displayed, as is shown in FIG. 10, or in 2-D plots as shown in FIGS. 9A-9C, or in another graphical format known in the arts. Also, impedance locus 5li can be utilized to characterize the ablation process, and can be used to perform vector analysis of RF or microwave current or other ablative energy vector (e.g. the magnitude and direction of the ablative energy), as well as vector analysis of physiologic indicators of cell necrosis, such as changes in interstitial conductivity. In various embodiments, the impedance locus 5li can be utilized to facilitate location and display of tumor volume 5", ablation volume 5av, or other desired tissue mass or volume, at the target tissue site. The generation and display of the impedance locus 5li (in 2-D or 3-D) can be configured to provide the medical practitioner an easily discernible visual cue as to the location, size, or movement of the ablation volume 5av, the tumor volume 5", or other selected tissue volume.

Referring to FIG. 1, in addition to identifying tissue types, monitoring device 19, along with impedance sensing arrays 22a, can also be employed to monitor in real time the progression of an ablative procedure, including the progression of an ablation volume 5av resulting from the delivery of energy to target tissue volume 5'. This reduces damage to tissue surrounding the targeted mass to be ablated. By monitoring the impedance at various points within and outside of the interior of tissue site 5', a determination of the selected tissue mass periphery can be made, as well as a determination of when cell necrosis is complete. If at any time sensor 22 determines that an impedance level or an ablation endpoint has been met or exceeded, then an appropriate feedback signal is inputted to power source 20, which then stops or otherwise adjusts the levels of ablative energy delivered to electrodes 18 and 18'. The target tissue site 5" can also be probed and interrogated by sensor array 22a after the completion of ablation, to confirm that ablation is complete for the entire desired ablation volume 5av. By probing the ablated region with sensor array 22a, the three-dimensional volume of the ablation 5av can be assessed, and the margin 5m of ablated healthy tissue beyond the tumor mass 5" can also be measured.

Figure 11:
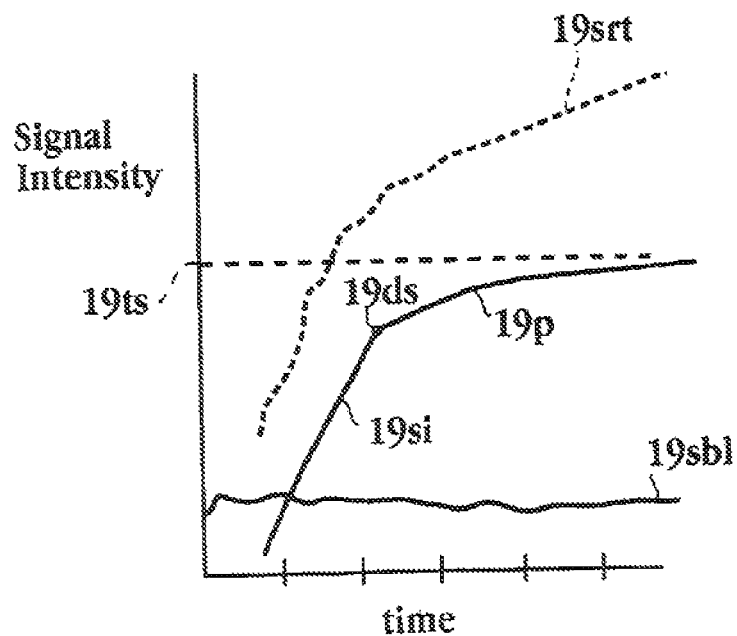
FIG. 11 is a plot of signal intensity verses time for a sample volume of ablating tissue, illustrating quantitative determinants of an ablation endpoint.
Figure 28:
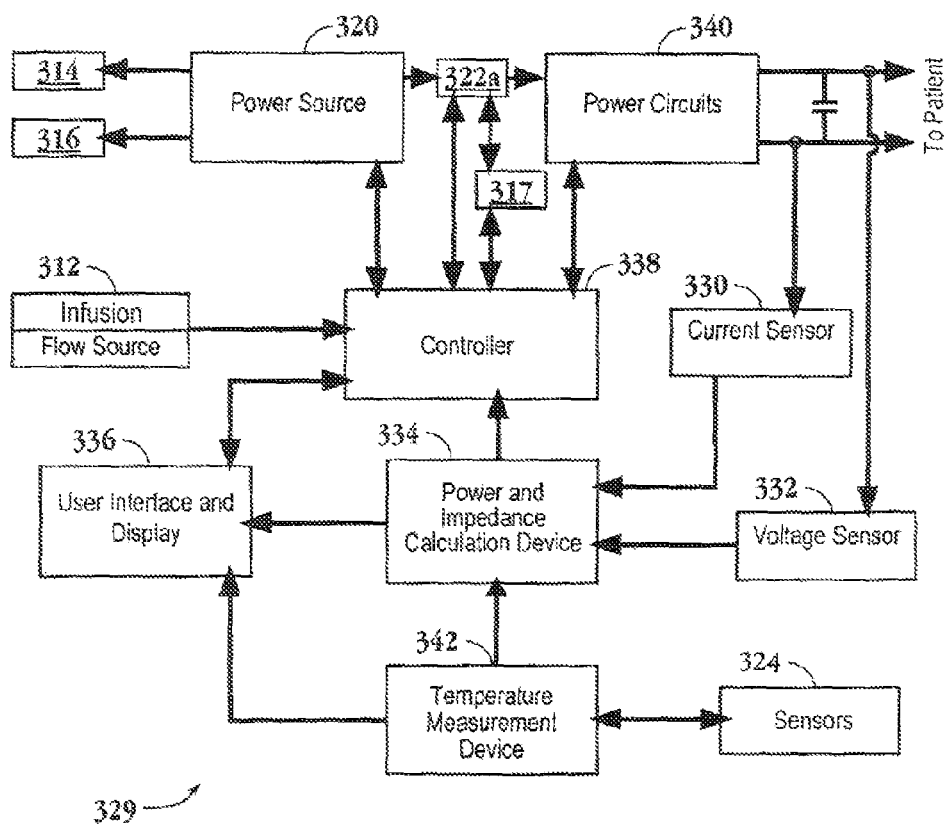
FIG. 28 is a block diagram illustrating components for a feedback control system.

Referring now to FIG. 11, in embodiment for monitoring the ablative process, the impedance signal intensity 19si for a sample volume of tissue 5sv bounded by two or sensing members 22m or array 22a can be monitored over time, using monitoring device 19, supply 20, or other bioelectric signal monitoring means known in the art. An endpoint for ablation can be determined, based on either a selectable threshold value 19ts of signal intensity 19si, or an inflection point or change in slope 19ds (e.g. a derivative) of the curve of signal intensity 19si, or a combination of both. In an embodiment, the signal intensity curve can comprise the subtraction of a baseline (or reference) impedance measurement 19sbl of a nearby, but non-ablated, tissue volume from a real time measurement 19srt of the target tissue volume 5" during the time course of ablation. This compensates for any signal or tissue hysteresis over time. Values for 19ts and 19ds can be input and stored in logic resource 19lr coupled to impedance monitoring 19 (FIG. 6), or incorporated into an electronic algorithm controlling the delivery of energy, which can be stored in a controller or processor 338 coupled to power supply 20 (FIG. 28).

Figure 12A:
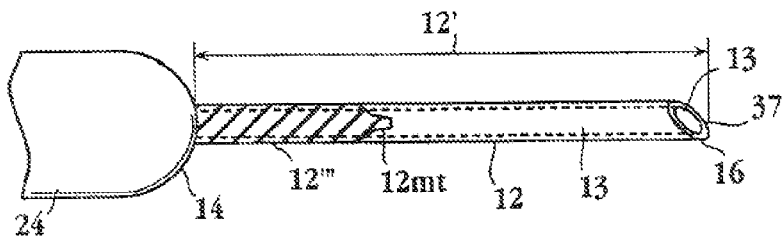
FIG. 12A is a lateral view illustrating an embodiment of the introducer.
Figure 12B:
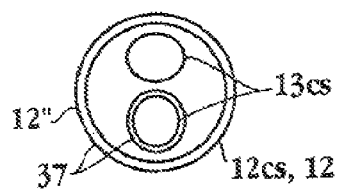
FIGS. 12B and 12C are cross sectional profiles of the introducer.
Figure 12C:
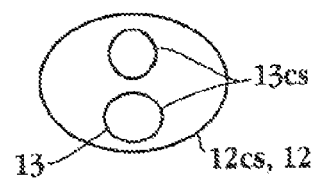
Figure 13:
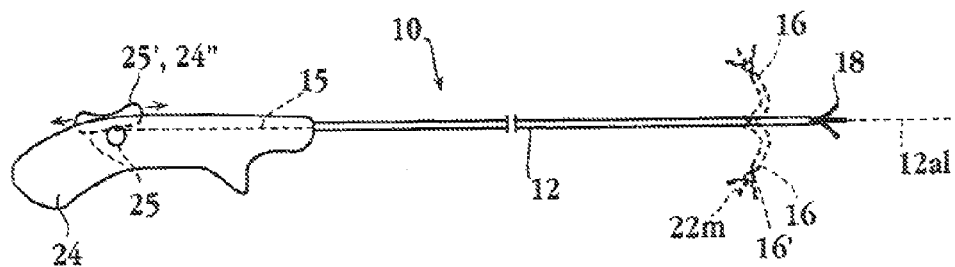
FIG. 13 is a lateral view of a deflectable introducer.

Turning now to FIGS. 12A-13 for a further discussion of introducer 12, in various embodiments, introducer 12 can be a trocar, a catheter, a multi-lumen catheter, a wire-reinforced or metal-braided polymer shaft, a port device, a subcutaneous port device, or other medical introducing device known to those skilled in the art. In various embodiments, introducer 12, as well as resilient member 18, can be configured to have varying mechanical properties along their respective lengths, including, but not limited to, variable stiffness, torquability, column strength, flexural modulus, pushability, trackability and other mechanical performance parameters known in the art. Referring to FIG. 12A, this can be achieved through the use of stiff shaft sections 12''' disposed within portions of introducer 12 along its length 12'. It can also be accomplished through the use of braids, varying/tapered diameters, and different materials (e.g. stiffer materials joined to flexible materials) positioned over portions of introducer 12. Sections 12''' made from different materials can be joined using introducer bonding methods known in the art, such as hot melt junctions (with or without capture tubes/collates), adhesive joints, butt joints, and the like. The joining method can be controlled/selected so as to control the mechanical transition 12mt between two sections 12''' to a desired gradient (e.g. smooth vs. abrupt). In related embodiments, introducer 12 and/or member 18 can be configured to have stiffer proximal portions and more flexible distal portions, so as to facilitate one or more of the following: (i) introducer steerability and positioning of distal tip 16 at a selectable target tissue site 5'; and (ii) reduced risk of perforation, abrasion and other trauma during the positioning the introducer 12 to the tissue site 5'. In various embodiments, the transition 12mt from the stiffer portion to the more flexible portion can be configured to be either gradual with a linear or curve-linear transition 12mt or a stepped or abrupt transition 12mt, or combinations thereof.

Referring to FIGS. 12B and 12C, introducer 12 can have a substantially circular, semicircular, oval, or crescent shaped cross sectional profile 12cs, as well as combinations thereof, along its length 12'. Similarly, lumens 13 can have a circular, semicircular, oval, or crescent shaped cross sectional profile 13cs for all or a portion of the length 12' of introducer 12.

Suitable materials for introducer 12 and resilient member 18 include, but are not limited to, stainless steel, shape memory alloys such as nickel titanium alloys, polyesters, polyethylenes, polyurethanes, PEBAX®, polyamides, nylons, copolymers thereof, and other medical plastics known to those skilled in the art. All or portions 12''' of introducer 12 can be coated with a lubricious coating or film 12" which reduces the friction (and hence trauma) of introducer 12 with hepatic, pulmonary, bone, and other tissue. Such coatings 12" can include, but are not limited to, silicones, PTFE (including TEFLON®), and other coatings known in the art. Also, all or portions of apparatus 10, including introducer 12 and members 18, can be constructed of materials known in the art that are optimized and/or compatible with radiation sterilizations (e.g. Gamma or E-beam). In related embodiments, all or portions of apparatus 10 can be configured (e.g. lumen diameter to length ratio, etc.) to be sterilized by plasma (e.g. $H_2O_2$) sterilization.

Referring now to FIG. 13, in other embodiments, all or portions of introducer 12 or resilient members 18 can be configured to be deflectable and/or steerable using deflection mechanisms 25, which can include pull wires 15, ratchets, cams, latch and lock mechanisms, piezoelectric materials, and other deflection means known in the art. The amount of deflection of introducer 12 is selectable, and can be configured to allow the maneuvering of introducer 12 through oblique turns in tissue, organs, organ ducts, and blood vessels. In specific embodiments, the distal portions of introducer 12 can be configured to deflect 0-180° or more in up to three axes 12al to allow the tip of introducer 12 to have retrograde positioning capability. Deflection mechanism 25 can be coupled to or integral with a movable or slidable actuator 24" on handpiece 24. Mechanism 25 and coupled actuator 25' are configured to allow the physician to selectively control the amount of deflection of distal tip 16 or other portion of introducer 12. Actuator 25' can be configured to both rotate and deflect distal tip 16 by a combination of rotation and longitudinal movement.

Figure 14:
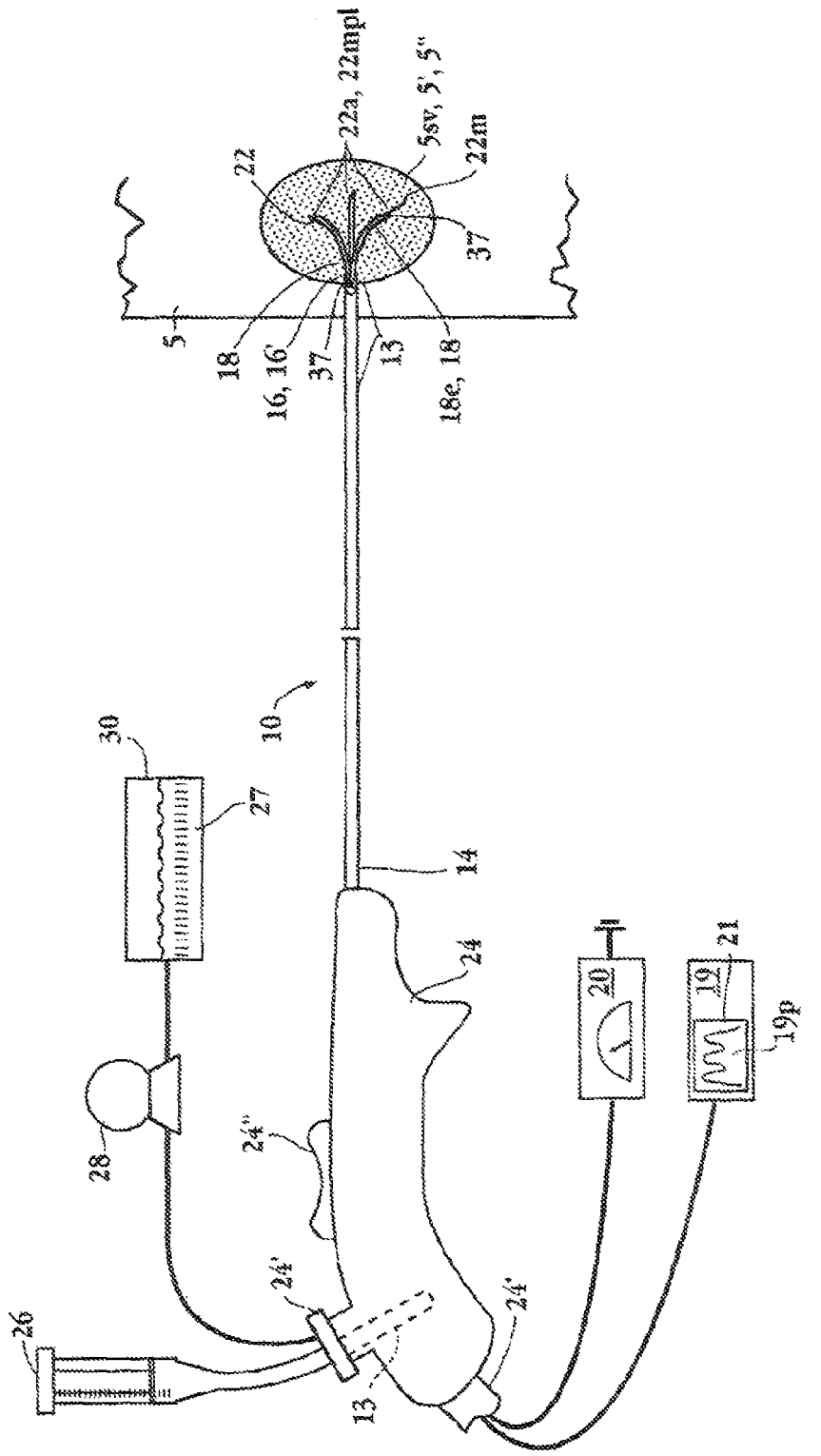
FIG. 14 is a lateral view of a tissue biopsy and treatment apparatus with a hand piece and coupled aspiration device, fluid delivery device, and fluid reservoir.
Figure 15A:
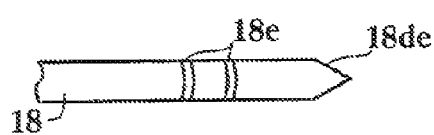
Figure 15B:
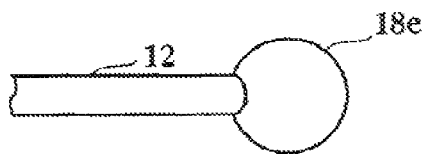
Figure 15C:
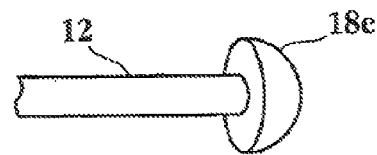
Figure 15D:
Figure 15E:
Figure 15F:
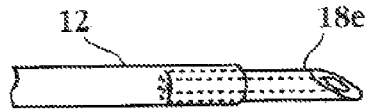
Figure 15G:
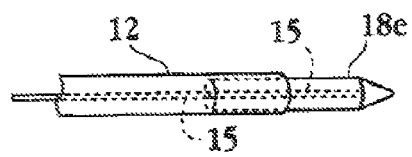
Figure 15H:
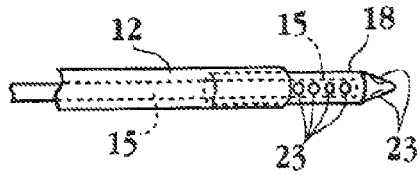

Referring now to FIG. 14, in various embodiments, introducer 12 can be coupled at its proximal end 14 to a handle 24 or handpiece 24. Handpiece 24 can be detachable and can include ports 24' and actuators 24". Ports 24' can be coupled to one or more lumens 13 (and in turn lumens 72) and can include fluid and gas ports/connectors and electrical, optical connectors. In various embodiments, ports 24' can be configured for aspiration (including the aspiration of tissue), and the delivery of cooling, electrolytic, irrigation, polymer and other fluids (both liquid and gas) described herein. Ports 24' can include, but are not limited to, luer fittings, valves (one-way, two-way), toughy-bourst connectors, swage fittings, and other adaptors and medical fittings known in the art. Ports 24' can also include lemo-connectors, computer connectors (serial, parallel, DIN, etc) micro connectors and other electrical varieties well known to those skilled in the art. Further, ports 24' can include opto-electronic connections which allow optical and electronic coupling of optical fibers and/or viewing scopes to illuminating sources, eye pieces, video monitors and the like. Actuators 24" can include rocker switches, pivot bars, buttons, knobs, ratchets, levers, slides, and other mechanical actuators known in the art, all or portion of which can be indexed. These actuators 24" can be configured to be mechanically, electro-mechanically, or optically coupled to pull wires, deflection mechanisms, and the like, allowing selective control and steering of introducer 12. Handpiece 24 can be coupled to tissue aspiration/collection devices 26, fluid delivery devices 28 (e.g. infusion pumps), fluid reservoirs 38 (cooling, electrolytic, irrigation, etc.), or power source 20, through the use of ports 24'. Tissue aspiration/collection devices 26 can include syringes and vacuum sources coupled to a filter or collection chamber/bag. Fluid delivery devices 28 can include medical infusion pumps, Harvard pumps, syringes, and the like. In specific embodiments, aspiration device 26 can be configured for performing thoracentesis.

Turning now to FIGS. 1, 2 and 14 for a discussion of resilient members 18 and sensing members 22m, these members can be of different sizes, shapes and configurations, with various mechanical properties selected for the particular tissue site 5'. In one embodiment, members 18 can be needles, with sizes in the range of 28 to 12 gauge, with specific embodiments of 14, 16 and 18 gauges. Resilient members 18 are configured to be in non-deployed positions while retained in introducer 12. In the non-deployed positions, resilient members 18 may be in a compacted state, spring loaded and generally confined within introducer 12, or substantially straight if made of a suitable memory metal such as nitinol. As resilient members 18 are advanced out of introducer 12, they become distended to a deployed state, as a result of their spring or shape memory, that collectively defines an ablative volume 5av, from which tissue is ablated. The selectable deployment of resilient members 18 can be achieved through one or more of the following: (i) the amount of advancement of resilient members 18 from introducer 12; (ii) independent advancement of resilient members 18 from introducer 12; (iii) the lengths and/or sizes of energy delivery surfaces of electrodes 18 and 18'; (iv) variation in materials used for electrodes 18 and 18'; (v) selection of the amount of spring loading or shape memory of electrodes 18 and 18'; and (vi) variation of the geometric configurations of electrodes 18 and 18' in their deployed states.

As described herein, in various embodiments, all or a portion of resilient member 18 can be an energy delivery device 18 or member 18e. Turning to a discussion of energy delivery device 18 and power sources 20, the specific energy delivery devices 18 and power sources 20 that can be employed include, but are not limited to, the following: (i) a microwave power source coupled to a microwave antenna, providing microwave energy in the frequency range from about 915 MHz to about 2.45 GHz; (ii) a radio-frequency (RF) power source coupled to an RF electrode; (iii) a coherent light source coupled to an optical fiber or light pipe; (iv) an incoherent light source coupled to an optical fiber; (v) a heated fluid coupled to a catheter, with a closed or at least partially open lumen configured to receive the heated fluid; (vi) a cooled fluid coupled to a catheter, with a closed or at least partially open lumen configured to receive the cooled fluid; (vii) a cryogenic fluid; (viii) a resistive heating source coupled to a conductive wire; (ix) an ultrasound power source coupled to an ultrasound emitter, wherein the ultrasound power source produces ultrasound energy in the range of about 300 KHZ to about 3 GHz; and (x) combinations thereof. For ease of discussion, for the remainder of this application, the energy delivery device 18 is one or more of RF electrodes 18e, and the power source 20 utilized is an RF power supply 20. For these and related embodiments, RF power supply 20 can be configured to deliver 5 to 200 watts, preferably 5 to 100, and still more preferably 5 to 50 watts of electromagnetic energy is to the electrodes 18e of energy delivery device 18, without impeding out. The electrodes 18e are electromagnetically coupled to energy source 20. The coupling can be direct, from energy source 20 to each electrode 18e respectively, or indirect, by using a collet, sleeve, and the like which couples one or more electrodes 18e to energy source 20.

Figure 16:
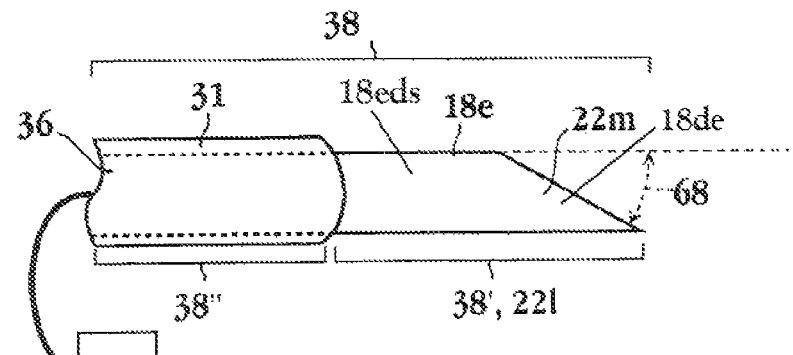
FIG. 16 is a lateral view illustrating a needle electrode configured to penetrate tissue.

In various embodiments, electrodes 18e, including impedance sensors 22 and sensing members 22m, can have a variety of shapes and geometries. Referring now to FIGS. 15A-15H, exemplary shapes and geometries can include, but are not limited to, ring-like, ball, hemispherical, cylindrical, conical, needle-like, and combinations thereof. Referring to FIG. 16, in an embodiment, electrode 18e can be a needle with sufficient sharpness to penetrate tissue, including fibrous tissue such as encapsulated tumors, cartilage, and bone. The distal end 18de of electrode 18e can have a cut angle 68 that ranges from 1 to 60°, with preferred ranges of at least 25°, or at least 30°, and specific embodiments of 25° and 30°. The surface of electrode 18e can be smooth or textured, and concave or convex. Electrode 18e can have different lengths 38' that are advanced from distal end 16' of introducer 12 (FIG. 2). The lengths 38' can be determined by the actual physical length 38 of electrode 18e, the length 38' of an energy delivery surface 18eds of electrode 18e, and the length 38" of electrode 18e that is covered by an insulator 36. Suitable lengths 38' include, but are not limited to, a range from 0.5-30 cm, with specific embodiments of 0.5, 1, 3, 5, 10, 15 and 25.0 cm. The conductive surface area 18eds of electrode 18e can range from 0.05 mm$^2$ to 100 cm$^2$. The actual lengths 38' of electrode 18e depend on the location of tissue site 5' to be ablated, its distance from the site, its accessibility, as well as whether or not the physician performs an endoscopic or surgical procedure. The conductive surface area 18eds depends on the desired ablation volume 5av to be created.

Figure 17:
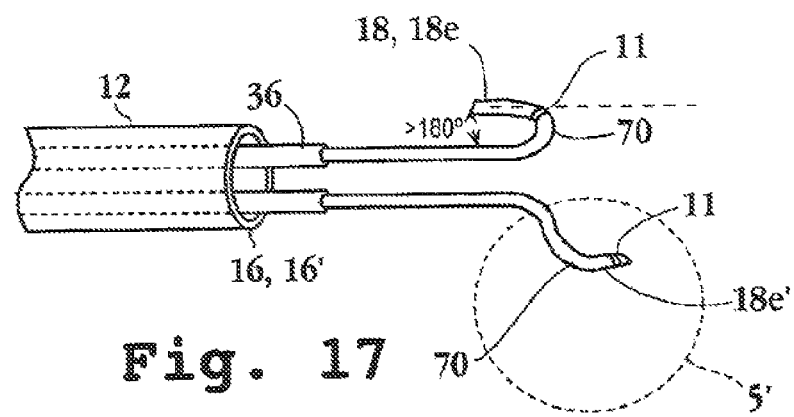
FIG. 17 is a lateral view illustrating electrodes having at least one radius of curvature.
Figure 18:
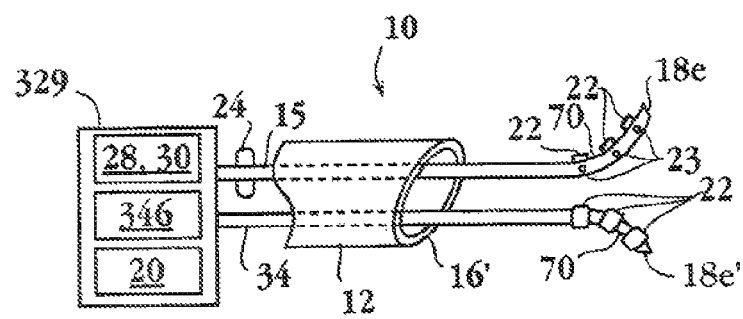
FIG. 18 is a lateral view illustrating electrodes having at least one radius of curvature, sensors, and a coupled advancement device.
Figure 19:
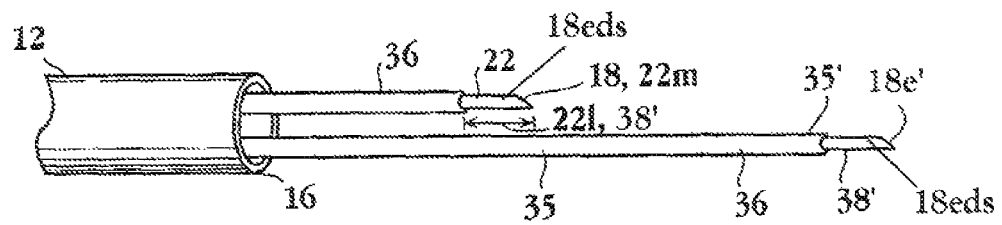
FIG. 19 is a perspective view illustrating insulation sleeves positioned at exterior surfaces of sensing members or resilient members so as to define an impedance sensor length or an energy delivery surface.

Referring now to FIGS. 17 and 18, electrodes 18e can also be configured to be flexible and/or deflectable, having one or more radii of curvature 70 which can exceed 180 degrees. In use, electrodes 18e can be positioned to heat, necrotize, or ablate any selected target tissue volume 5'. A radiopaque marker 11 can be coated on electrodes 18e for visualization purposes. Electrodes 18e can be coupled to introducer 12, and/or an advancement member or device 15, or an advancement-retraction member 34, using soldering, brazing, welding, crimping, adhesive bonding, and other joining methods known in the medical device arts. Also, electrodes 18e can include one or more coupled sensors 22 to measure temperature and impedance (both of the electrode and of the surrounding tissue), voltage and current, or other physical properties of the electrodes 18e and adjacent tissue. Sensors 22 can be at exterior surfaces of electrodes 18e at their distal ends or intermediate sections.

Electrode 18e can be made of a variety of conductive materials, both metallic and non-metallic. Suitable materials for electrode 18e include, steel such as 304 stainless steel of hypodermic quality, platinum, gold, silver, alloys, and combinations thereof. Also, electrode 18e can be made of conductive, solid or hollow, straight wires of various shapes, such as round, flat, triangular, rectangular, hexagonal, elliptical, and the like. In a specific embodiment, all or portions of electrodes 18e, or a second electrode 18e', can be made of a shaped memory metal, such as NiTi, commercially available from Raychem Corporation, Menlo Park, Calif.

Referring now to FIGS. 19 through 22, in various embodiments, one or more resilient members 18 or electrodes 18e can be covered by an insulative layer 36, so as to have an exterior surface that is wholly or partially insulated, and provide a non-insulated area which is an energy delivery surface 18eds. In an embodiment, shown in FIG. 19, insulative layer 36 can comprise a sleeve that can be fixed, or slidably positioned, along the length of electrode 18e to vary and control the length 38' of energy delivery surface 18eds. Suitable material for insulative layer 36 includes polyamide and fluorocarbon polymers, such as TEFLON®.

Figure 20:
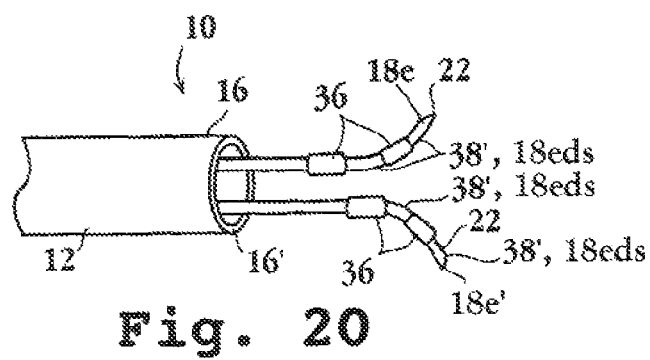
FIG. 20 is a perspective view illustrating electrodes with multiple insulation sleeves that circumferentially insulate selected sections of the electrodes.
Figure 21:
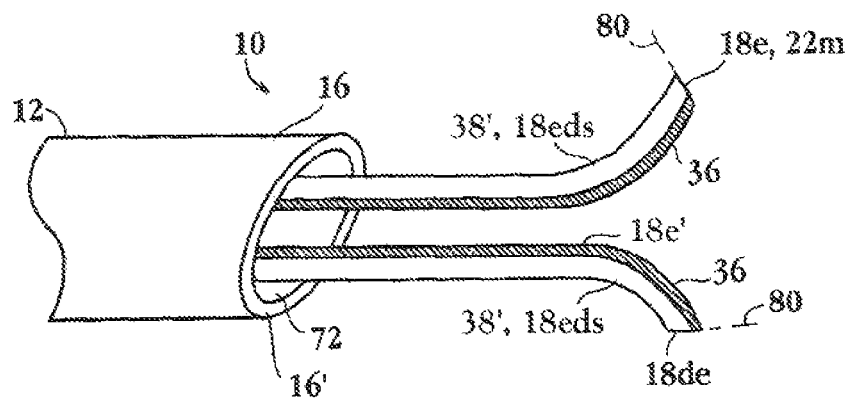
FIG. 21 is a perspective view illustrating electrodes with insulation that extends along longitudinal sections to define adjacent longitudinal energy delivery surfaces.
Figure 22:
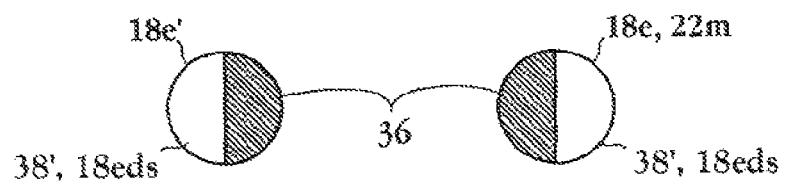
FIG. 22 is a cross-sectional view of the embodiment of FIG. 21.

In the embodiment shown in FIG. 20, insulation 36 is formed at the exterior of electrodes 18e in circumferential patterns, leaving a plurality of energy delivery surfaces 18eds. In an embodiment, shown in FIGS. 21 and 22, insulation 36 extends along a longitudinal exterior surface of electrodes 18e. Insulation 36 can extend along a selected distance along a longitudinal length of electrodes 18e, and around a selectable portion of a circumference of electrodes 18e. In various embodiments, sections of electrodes 18e can have insulation 36 along selected longitudinal lengths, as well as completely surround one or more circumferential sections of electrodes 18e. Insulation 36 positioned at the exterior of electrodes 18, 18e can be varied to define any desired shape, size and geometry of energy delivery surface 18eds.

Figure 23:
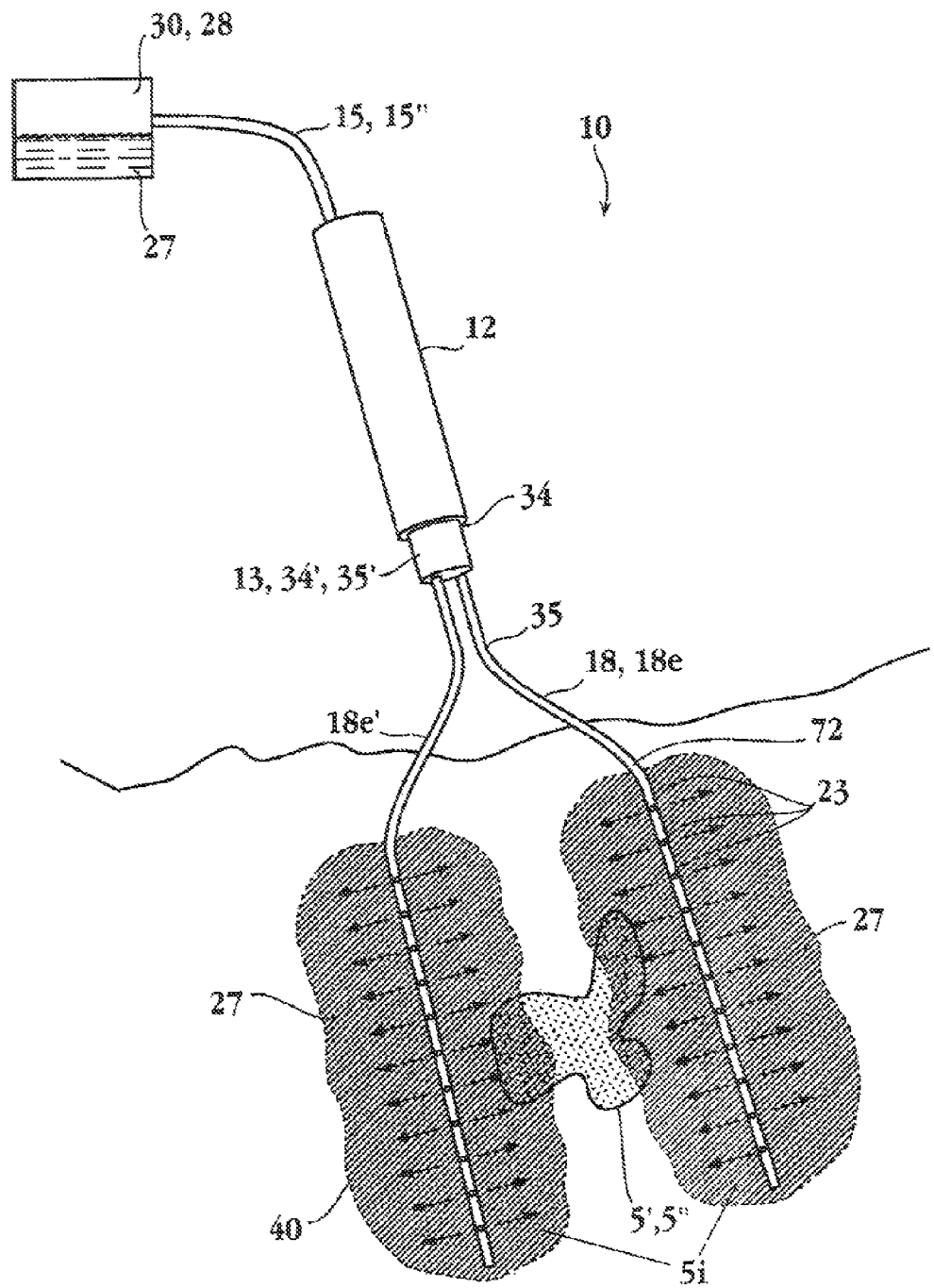
FIG. 23 is a lateral view of an apparatus with electrodes having a lumen and apertures configured for the delivery of fluid, and the use of infused fluid to create enhanced electrodes.

Referring now to FIG. 23, in various embodiments, electrode 18e can include one or more lumens 72 (which can be contiguous with, or the same as, lumen 13) coupled to a plurality of fluid distribution ports 23 (which can be apertures 23), from which a variety of fluids 27 can be introduced, including conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media, and combinations thereof. This is accomplished by having ports or apertures 23 that are fluidically coupled to one or more of lumens 72 or coupled to lumens 13, which in turn coupled to fluid reservoir 30 and/or fluid delivery device 28.

In an embodiment, shown in FIG. 23, a conductivity enhancing solution 27 can be infused into target tissue site 5' including tissue mass 5". The conductivity enhancing solution can be infused before, during, or after the delivery of energy to the tissue site 5' by the energy delivery device 10. The infusion of a conductivity enhancing solution 27 into the target tissue site 5' creates an infused tissue area 5i that has an increased electrical conductivity (verses un-infused tissue), so as to act as an enhanced electrode 40. During RF energy delivery, the current densities in enhanced electrode 40 are greatly lowered, allowing the delivery of greater amounts of RF power into electrode 40 and target tissue site 5' without impedance failures. In use, the infusion of the target tissue site 5' with conductivity enhancing solution 27 provides two important benefits: (i) faster ablation times, and (ii) the creation of larger lesions, both without impedance-related shut downs of the RF power supply. This is due to the fact that the conductivity enhancing solution 27 reduces current densities and prevents desiccation of tissue adjacent the electrodes 18, 18e, 18e' that would otherwise result in increases in tissue impedance. A preferred example of a conductivity enhancing solution 27 is a hypertonic saline solution. Other examples include halide salt solutions, colloidal ferro solutions, and colloidal silver solutions. The conductivity of enhanced electrode 40 can be increased by control of the rate and amount of infusion, and by the use of solutions with greater concentrations of electrolytes (e.g. saline) and hence greater conductivity. In various embodiments, the use of conductivity enhancing solution 27 allows the delivery of up to 2000 watts of power into the tissue site 5' without impedance shut down, with specific embodiments of 50, 100, 150, 250, 500, 1000 and 1500 watts, achieved by varying the flow, amount and concentration of infusion solution 27. The infusion of solution 27 can be continuous, pulsed, or combinations thereof, and can be controlled by a feedback control system described herein. In a specific embodiment, a bolus of infusion solution 27 is delivered prior to energy delivery, followed by a continuous delivery initiated before or during energy delivery with energy delivery device 18 or other means.

Figure 24:
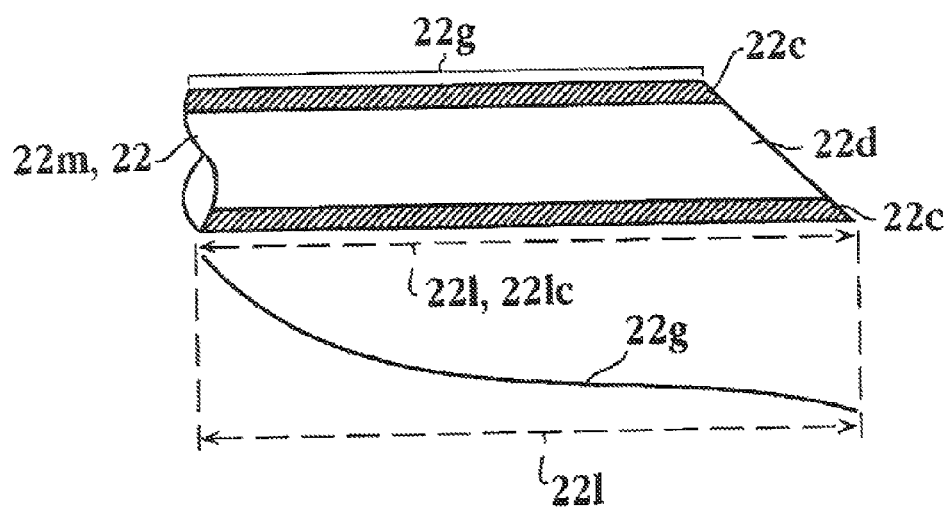
FIG. 24 is a perspective view of an impedance-sensing member that includes a conductive coating that can be configured to produce an impedance gradient along the sensing member.

Turning now to a discussion of impedance sensors 22, in various embodiments, impedance sensors 22 can include all or a portion of resilient members 18. Referring back to FIG. 19, when resilient member 18 is made of a conductive material, the length 22l of impedance sensor 22 or sensing member 22m can be defined by the placement of a slidable or fixed insulative layer 36. Also, in various embodiments, impedance sensors 22 can be fabricated from a variety of conductive materials and metals known in the art, including stainless steel, copper, silver, gold, platinum, alloys, and combinations thereof. Referring now to FIG. 24, similarly, all or portions of sensors 22 or sensor members 22m can comprise a conductive coating 22c that is coated or deposited onto a selected portion of member 18. In various embodiments, coating 22c can comprise a conductive metal or conductive polymer coating known in the art that is applied using known methods, such as sputtering, vacuum deposition, dip coating, photolithography, and the like. In related embodiments, impedance sensing members 22m and/or sensors 22 can be configured to have a resistance gradient 22g along all or portions of their lengths 22l. The resistance gradient 22g can be increasing or decreasing in a linear, second order, third order, exponential, or other fashion. In a specific embodiment, the resistance gradient 22g is configured to compensate for resistance losses (i.e. of voltage) and/or hysteresis occurring along the length 22l of member 22m or sensor 22, as well as changes in the overall resistance of sensor 22 due to changes in the temperature and/or conducting/sensing length 22lc (and area) of sensor 22, as might occur due to advancement or retraction of slidable insulation layer 36, or fowling of the sensor 22 with desiccated, burnt tissue or otherwise adherent tissue. In this and related embodiments, the gradient 22g can be so configured to produce the least resistance (e.g. maximum conductance) at the distal tip 22d of the sensor 22, and increasing resistance moving in a proximal direction along the sensor 22 or sensing member 22m. The gradient 22g can be produced via the use of coating 22c by varying either the thickness or the composition of the coating 22c, or a combination of both, along the length 22l of the sensor 22, using methods known in the art. Further, by compensating for such resistance changes or losses along the length or area of impedance sensor 22, these and related embodiments also improve the measurement and detection of real and imaginary components of complex impedance. In other related embodiments, the resistance gradient 22g can be in a radial direction, or a combination of radial and linear directions, with respect to the sensor length 22l.

In other embodiments, sensors 22 can comprise a number of biomedical sensors known in the art, including, but not limited to, thermal sensors, acoustical sensors, optical sensors, pH sensors, gas sensors, flow sensors, positional sensors, and pressure/force sensors. Thermal sensors can include thermistors, thermocouples, resistive wires, and the like. Acoustical sensors can include ultrasound sensors, including piezoelectric sensors, which can be configured in an array. Pressure and force sensors can include strain gauge sensors, including silicon-based strain gauges.

In an embodiment, sensor 22 can be selected to measure temperature along with impedance to compensate for any temperature related bias or hysteresis in the impedance measurement. Accordingly, in an embodiment illustrated in FIG. 28, a feedback signal from a temperature sensor 329 or temperature calculation device 342 can be inputted to the impedance calculation device 334, described herein, to compensate for such variations. Temperature monitoring can also be used to perform real time monitoring of ablative energy delivery. If at any time sensor 22 determines that a desired cell necrosis temperature is exceeded, then an appropriate signal can be sent to power control circuitry 340, describe herein, to reduce or regulate the amount of electromagnetic energy delivered to electrodes 18 and 18'.

Figure 25A:
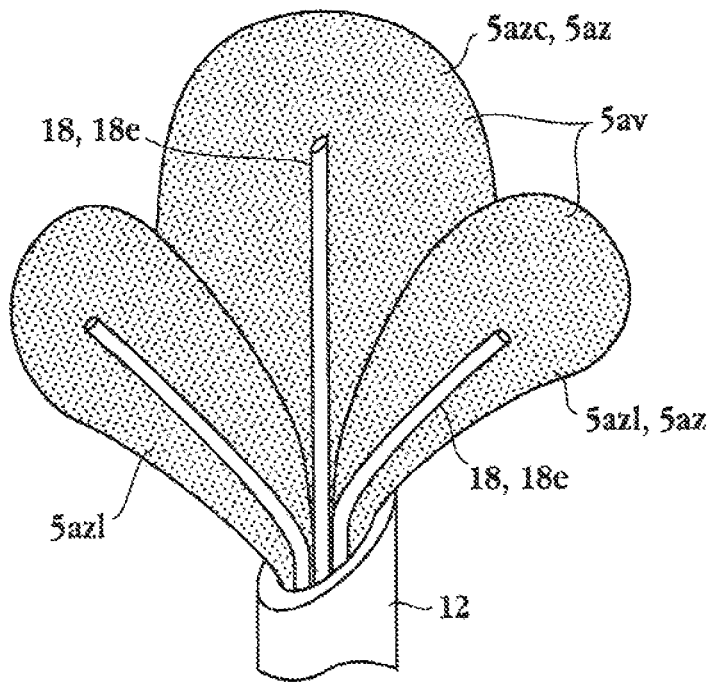
FIGS. 25A-25C are perspective views of energy delivering ablation apparatuses using frequency controlled positionable ablation fields.
Figure 25B:
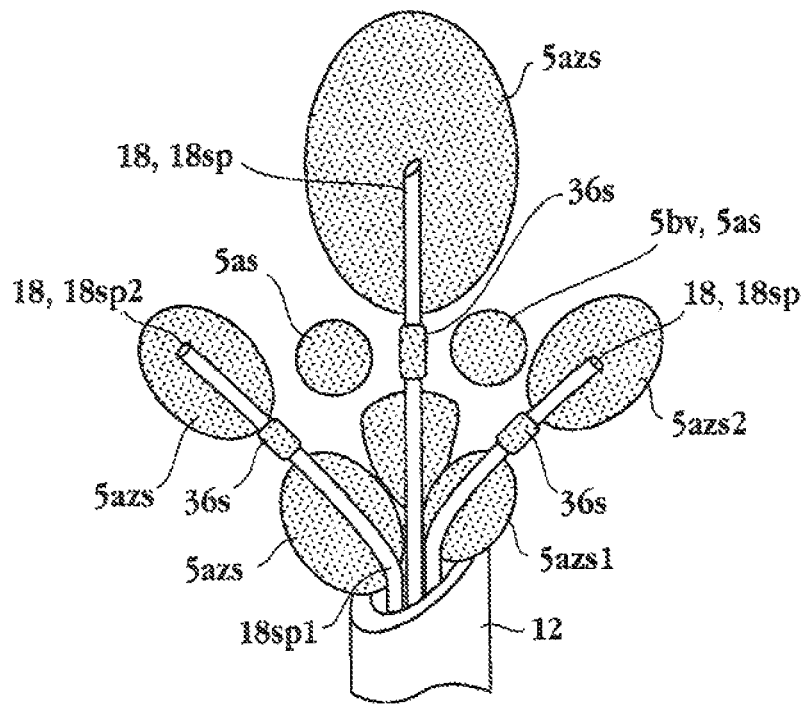
Figure 25C:
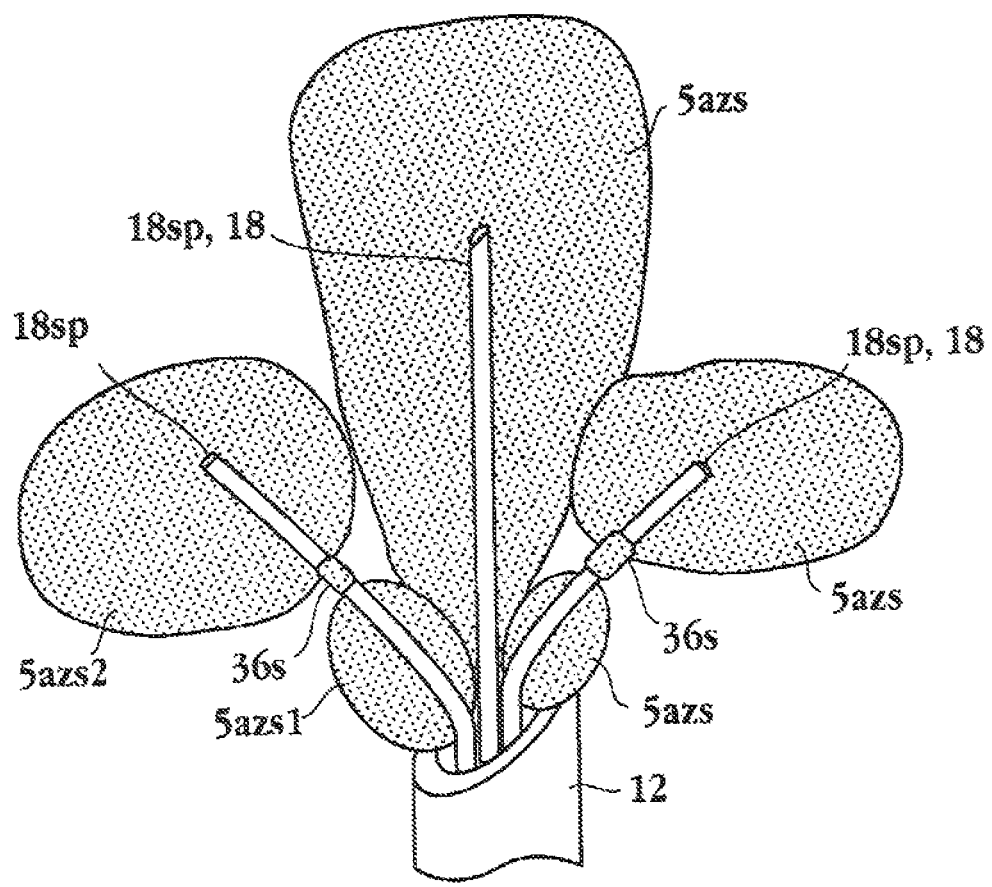
Figure 26A:
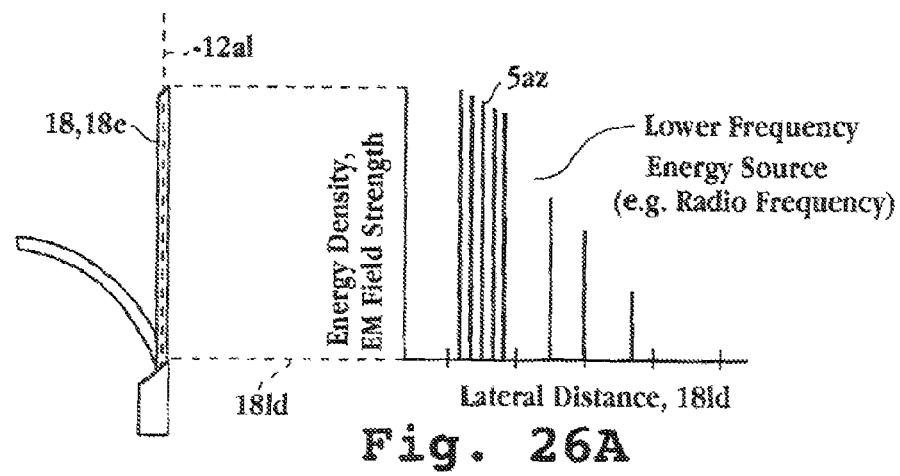
Figure 26B:
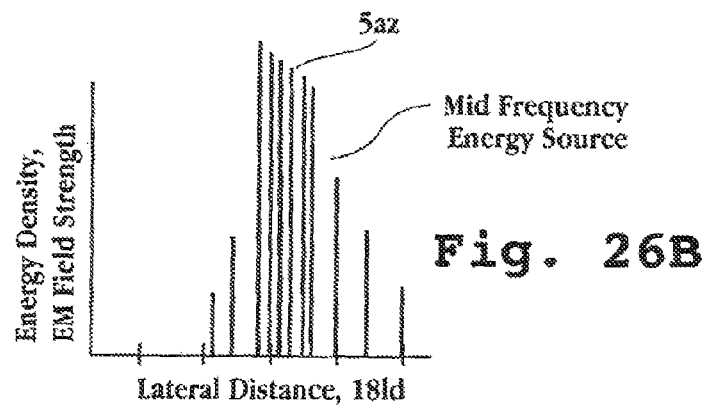
Figure 26C:
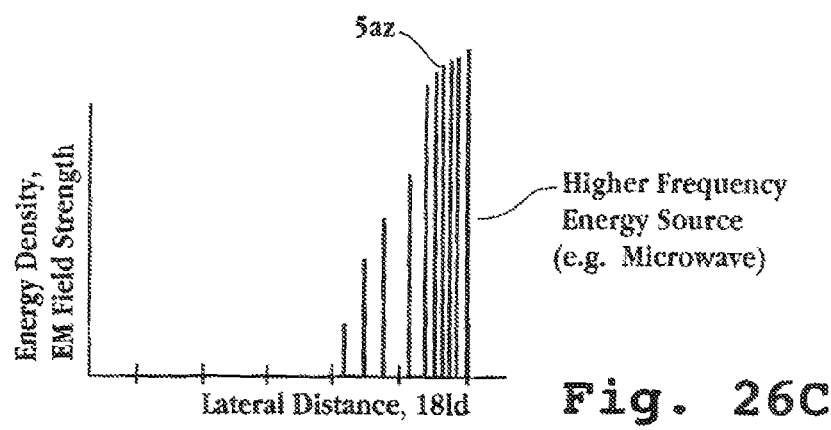

Referring now to FIGS. 25A-25C and 28A-26C, in an embodiment, the position and size of an ablation volume 5av produced by the delivery of electromagnetic energy can be controlled via the frequency of the ablative energy delivered to one or more electrodes 18e or energy delivery devices 18. As shown in FIG. 26A, lower electromagnetic frequencies, such as RF frequencies (e.g. 1 kHz to 1 MHZ), produce a more localized energy concentration (e.g. current density), with the resulting zone of energy concentration or ablation zone 5az occurring close to the energy delivery electrode/antenna 18, 18e in terms of a lateral distance 18ld or other direction. As shown in FIGS. 26B and 26C, higher frequencies, such as microwave frequencies, result in a progressively more distant energy concentration and resulting ablation zone 5az. As shown in FIGS. 25A-25C, by varying the frequency of the delivered energy and/or utilizing energy delivery electrodes/antenna coupled to different frequency energy source (e.g. microwave vs. RF), the position, shape, and size of the resulting lesion can be precisely controlled and even steered. This can be accomplished by electrically isolating one or more electrodes 18 to allow for the use of separate frequencies for each electrode. Further, one or more isolated electrodes can be coupled to multiplexing circuitry, and/or control resources coupled to the power sources and individual electrodes/antenna. Such circuitry and control resources can be used to turn individual electrodes or antenna off and on as well as control/set the frequency of each. In use, these and related embodiments provide the benefit of allowing the size, position and shape of the lesion to be precisely controlled and/or titrated to meet the therapeutic needs of the target tissue.

Referring now to FIGS. 25B and 25C, in various embodiments, one or more electrodes 18 can have segmented portions 18sp so as to allow the electrodes 18 to emit or radiate energy at different wavelengths from different segmented portions 18sp of electrode 18. Segmentation can be achieved through the use of electrically insulated sections 36s.

In an embodiment, shown in FIG. 25B, the use of segmented electrodes 18sp allows the creation of segmented ablation zones 5azs, including a first and second segmented zone 5azs1 and 5azs2. The size and shape of the segmented ablation zones 5azs can be controlled by controlling the frequency of the delivered energy to each electrode segmented portion 18sp. The segmented ablation zones 5azs can also be configured to be discontinuous or overlapping. Such embodiments also provide the ability to avoid injury to anatomical structure such as blood vessels, nerves etc., which lie in close proximity or are actually surrounded by the tumor to be treated. For example, in an embodiment shown in FIG. 25, the segmented ablation zones 5azs1 and 5azs2 can be sized and positioned to have sufficient space between each zone to avoid damaging a blood vessel 5bv or other critical structure 5as which lies between two or more electrodes 18. Alternatively, if desired, the ablative frequencies delivered to each electrode segmented portion 18sp can be reconfigured to produce overlapping segmented ablation zones 5azs, as shown in FIG. 25C.

In use, the medical practitioner would position the apparatus, and then image the target tissue site (using imaging systems known in the art, such as ultrasound to identify both the tumor and critical structures, and then utilize that image to control the input frequency to the energy delivery device, to produce the desires lesion size and shape to completely ablate the tumor while avoiding the critical structure. In an embodiment, the image could be electronically stored and analyzed to identify tumors and surrounding anatomy (using imaging processing methods known in the art, such as edge detection algorithms, resident within a processor of the imaging device), with the output fed into a power control software module coupled to the power supply that controls the power frequency to produce the desired ablation volume. Another benefit of these and related embodiments is the ability to produce an energy or thermal gradient within a target tissue site. That is the ability to deliver more or less energy to discrete sections of the target tissue volume, in order to titrate the delivery of energy, to address the physical and thermal conditions of a particular tumor mass, and even subsections of the tumor mass. This is an important capability, because tumors are often morphologically, and therefore thermally, non-homogeneous, a problem which current ablative therapies have not recognized or addressed.

Exemplary embodiments for the use of this capability include delivering larger amounts of energy to the center of a tumor and less to the periphery, in order to produce higher temperatures and ensure complete ablation at the center and minimize risk of thermal injury to surrounding healthy tissue. Alternatively, increased energy could also be selectively directed to the tissue tract made by the RF needle or probe for other penetrating energy delivery device 18) in penetrating the tumor and surrounding tissue, to ensure that no living malignant tissue is dragged back through the tract upon removal of the RF needle.

Figure 27:
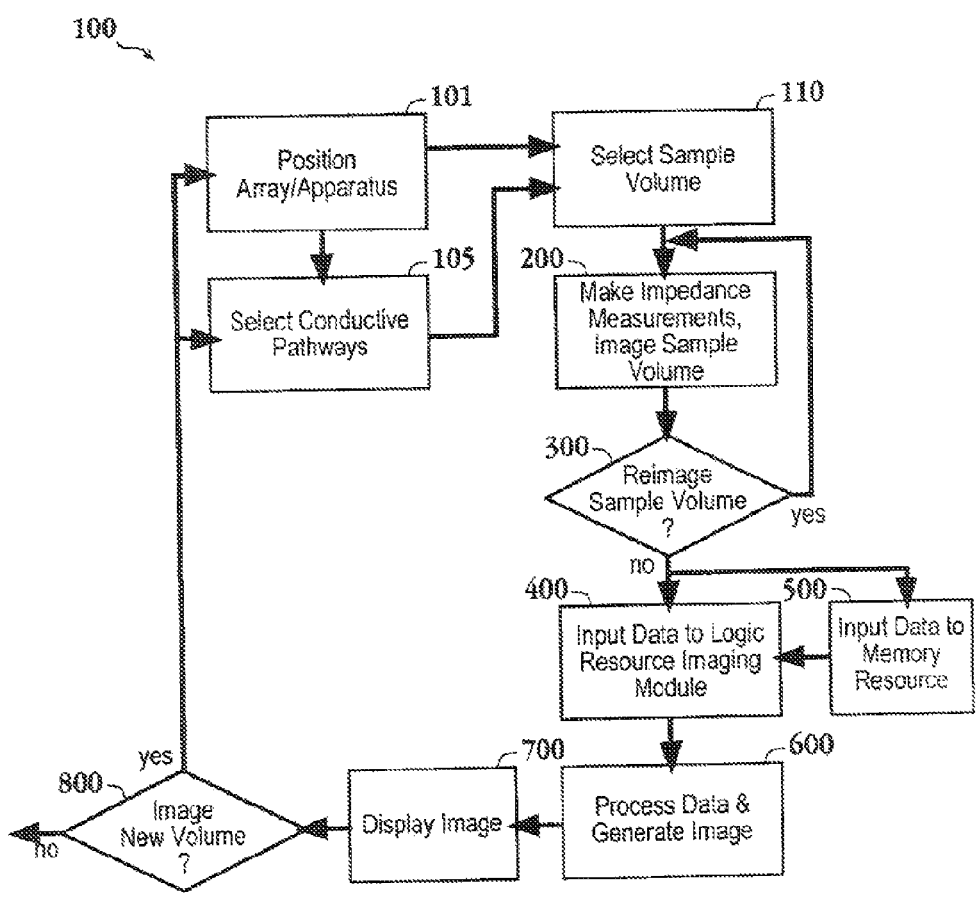
FIG. 27 is a flow chart illustrating a method for generating and displaying impedance derived images.

Referring now to FIGS. 6 and 27, various embodiments can be configured to generate and display images or maps 4' from one or more impedance measurements, including, but not limited to, complex impedance, impedance vectors, impedance loci, and combinations thereof. In an embodiment, a process 100 for generating and displaying an impedance map or impedance derived image 4' includes one or more of the following steps, all or a portion of which can be implemented as an electronic instruction set on a processor or logic resources described herein. Impedance array 22a and/or apparatus 10 can be positioned 101 within or near the desired sample volume 5sv, and/or conductive paths 22cp can be selected 105, so as to define and thus select 110 a particular sample volume 5sv. The volume 5sv is then imaged 200, using impedance measurements from all or a portion of the sensing members 22m or sensors 22 that comprise array 22a. A decision 300 can then be made to perform one or more re-imaging of the sample volume 5sv, in order to enhance image resolution as needed. Further, different excitation currents 20e can be applied to the target tissue site 5 and the voltage measurements repeated over time to increase measurement accuracy and precision, through increased sampling and reducing signal bias or noise that may occur at a particular excitation current 20e. Signals 22i from impedance array 22a can then be signaled or inputted 400 to logic resources 19lr, include module 19m, which can include an image processing sub-module 19mi. Sub-module 19mi includes subroutines or algorithms configured to generate an impedance map or derived image 4' of all or a portion of the target tissue site 5', using image/signal processing methods including, but not limited to, edge detection, filtering, approximating techniques, volume imaging, contrast enhancement, fuzzy logic, and other methods known in the art. One or more signals 22i from array 22a can be inputted or signaled 500 to memory resources 19mr (or an externally coupled data storage device) and stored as an impedance data set 22ds in memory resources 19mr. Subsequently, all or a portion of data set 22ds can be inputted to sub-module 19mi and processed 600, as described herein, to generate an impedance map or impedance derived image 4', which can then be displayed 700 on display device 21 or other display means. A decision 800 can then be made to image a new sample volume 5sv, and the process 100 can be repeated, starting at steps 101 or 105. In an embodiment, the imaging or mapping process 100 can be facilitated by rotating array 22a about introducer axis 12al, or by advancing and retracting one or more sensing members 22$m$ from members 18, or by a combination of both.

In an embodiment, module 19$m$ or 19$ml$ can include an algorithm utilizing Laplace's equation to calculate impedivity or resistivity from the known voltages and currents measured at one or more conductive pathways 22$cp$ within the target tissue site 5'. Reference measurements or normalization methods may be used to account for noise in the measurements. In related embodiments, impedance and other bioelectric measurements described herein can be analyzed and converted from the frequency domain to the time domain using transform functions, including Fourier transforms, fast Fourier transforms, wavelet analysis methods, and other numerical methods known in the art. These functions and methods can be incorporated into algorithms or subroutines within module 19$m$ or 19$mi$. These algorithms incorporating wavelet functions and transforms (including packets) can be configured to analyze and solve multidimensional and multifrequency data and associated functions and equations. This approach provides the benefit of more flexibility in applying wavelets to analyze impedance, conductivity and other bioelectric data gathered using systems and apparatus of the present application. One or more of the following wavelet functions can be incorporated into an algorithm or subroutine of module 19$m$ or 19$mi$: spline wavelets, waveform modeling and segmentation, time-frequency analysis, time-frequency localization, fast algorithms and filter banks, integral wavelet transforms, multiresolution analysis, cardinal splines, orthonormal wavelets, orthogonal wavelet spaces, wavelets of Haar, Shannon, and Meyer; spline wavelets of Battle-Lemari and Stromberg; the Daubechies wavelets; biorthogonal wavelets, orthogonal decompositions and reconstruction; and multidimensional wavelet transforms. In an exemplary embodiment, modules 19$m$ or 19$mi$ utilize spline wavelets to allow analysis and synthesis of discrete data on uniform or non-uniform tissue sample sites without any boundary effect.

Image module 19$mi$ can also include subroutines to perform interpolation, such as linear, quadratic, or cubic spline interpolation between individual measured impedance values from image data set 22$ds$ of a given sample volume 5$sv$. This improves image quality, including resolution, without any substantial loss of spatial or contrast detail. In related embodiments, the image processing module 19$mi$ can be configured to allow the user to select both the interpolative or other image processing algorithms to be performed, as well as the area of the image to be so processed. Thus, the user can select all or a portion of the image to be enhanced, providing faster image processing times (by not having to process the entire image) as well as improving image quality and other overall usability of the imaging apparatus/system. The image processing module 19$mi$ can also include gray scale and color contrast capabilities, which can be selectable. Both the gray scale and color contrast can be scaled or normalized against a baseline measurement obtained from the individual patient, a calibration measurement or a statistic (e.g. mean) value for a patient sample group, or a parameter (e.g. average) for a patient population, or a combination thereof.

In related embodiments, monitoring apparatus 19 and module 19$mi$ can be configured to generate impedance images with the maximum visual distinction or contrast between tumorous tissue and healthy tissue. This can be accomplished by using the frequency or combination of frequencies that yield the maximum sensitivity for selected tissue types or tissue conditions indicative of a tumor (e.g. degree of vascularity temperature etc). In an embodiment, such frequencies can be determined by performing swept frequency measurements and generating an impedance map or image using one or more frequencies, which result in the best contrast between healthy tissue and tumorous tissue or other tissue condition (e.g. thermal injury, necrosis etc.).

Figure 29:
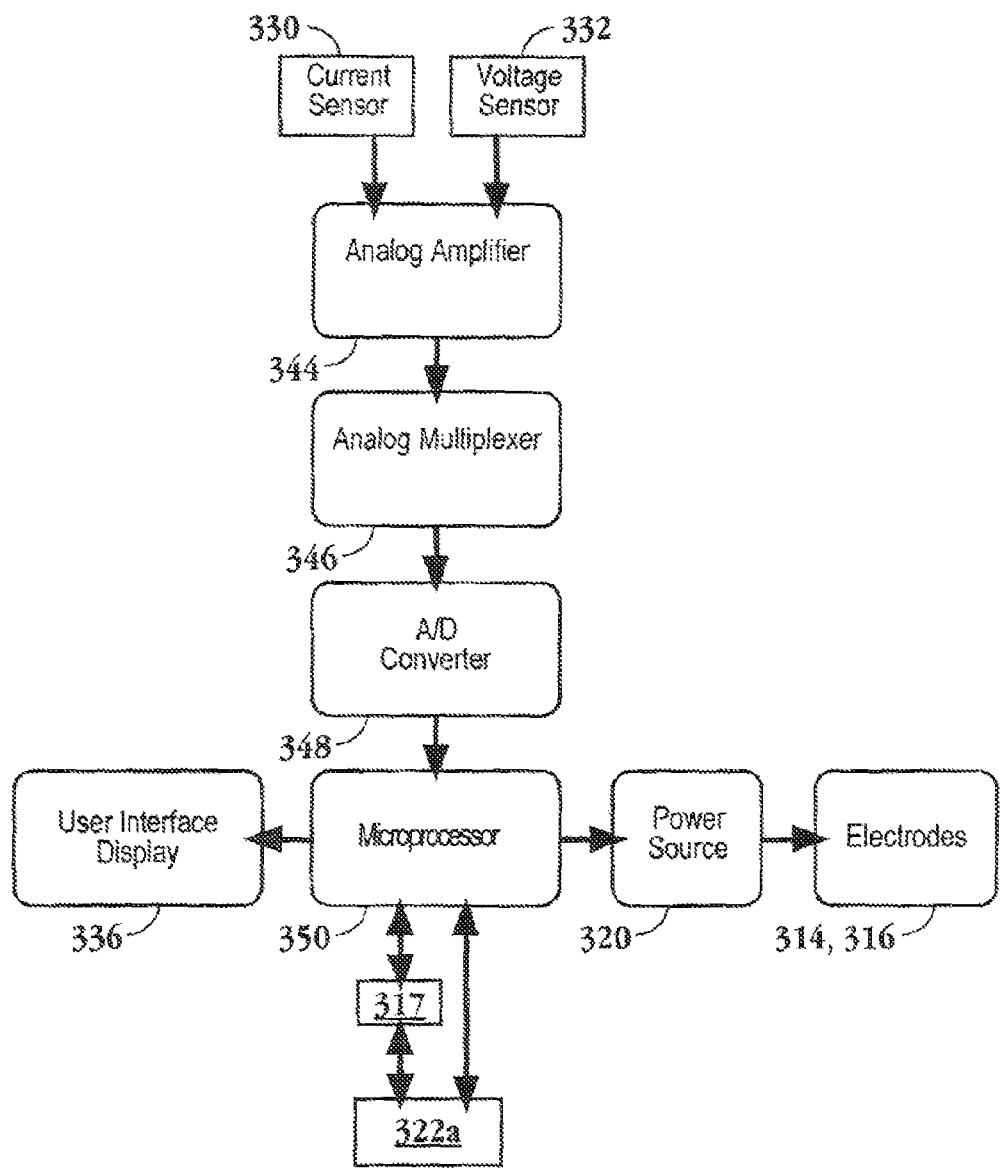
FIG. 29 is a block diagram illustrating components for a control system.

Referring now to FIGS. 28 and 29, a feedback control system 329 can be connected to energy source 320, sensors 324, impedance array 322$a$, and energy delivery devices 314 and 316. Feedback control system 329 uses temperature or impedance data from sensors 324 or array 322$a$ to modify the amount of electromagnetic energy received by energy delivery devices 314 and 316 from an initial setting of ablation energy output, ablation time, temperature, and current density (the "Four Parameters"). Feedback control system 329 can automatically change any of the Four Parameters. Feedback control system 329 can detect impedance or temperature and change any of the Four Parameters in response to either or a combination thereof. Feedback control system 329 can include a multiplexer (digital or analog) to multiplex different electrodes, sensors 324, and sensor arrays 322$a$, a temperature measurement device 342 or an impedance calculation device 334 that provides a control signal representative of temperature or impedance detected at one or more sensors 324 or array 322$a$. A microprocessor can be connected to the temperature control circuit.

The following discussion pertains particularly to the use of RF energy as an ablative energy source for apparatus 10. For purposes of this discussion, energy delivery devices 314 and 316 will now be referred to as RF electrodes/antennas 314 and 316, and energy source 320 will now be referred to as an RF energy source 320. However, it will be appreciated that all other energy delivery devices and sources discussed herein are equally applicable, and devices similar to those associated with treatment apparatus 10 can be utilized with laser optical fibers, microwave devices, and the like. The temperature of the tissue or of RF electrodes 314 and 316 is monitored, and the output power of energy source 320 is adjusted accordingly. The physician can, if desired, override the closed or open loop system.

The user of apparatus 10 can input an impedance value that corresponds to a setting position located at apparatus 10. Based on this value, along with measured impedance values, feedback control system 329 determines an optimal power and time needed in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline setting first. Larger lesions can be obtained by extending the time of ablation after a center core is formed at the baseline setting. The completion of lesion creation can be checked by advancing energy delivery device 316 from distal end 16' of introducer 12 to a position corresponding to a desired lesion size and monitoring the temperature at the periphery of the lesion such that a temperature sufficient to produce a lesion is attained.

The closed loop system 329 can also utilize a controller 338 to monitor the temperature, adjust the RF power, analyze the result, re-feed the result, and then modulate the power. More specifically, controller 338 governs the power levels, cycles, and duration that the RF energy is distributed to electrodes 314 and 316, to achieve and maintain power levels appropriate to achieve the desired treatment objectives and clinical endpoints. Controller 338 can also, in tandem, analyze spectral profile 19$p$ and perform tissue identification and ablation monitoring functions, including endpoint determination. Further, controller 338 can, in tandem, govern the delivery of electrolytic or cooling fluids, and the removal of aspirated tissue. Controller 338 can be integral to, or otherwise coupled to, power source 320. In this and related embodiments, controller 338 can be coupled to a separate impedance measurement current source 317, and can be configured to synchronize the delivery of pulsed power to tissue site 5', to allow for sensing by sensors 324 or sensor array 322a during power off intervals, to prevent or minimize signal interference, artifacts or unwanted tissue effects during sampling by sensors 324 or sensor array 322a. The controller 338 can also be coupled to an input/output (I/O) device, such as a keyboard, touchpad, PDA, microphone (coupled to speech recognition software resident in controller 338 or other computer), and the like. In an embodiment, current source 317 can be a multi-frequency generator, such as those manufactured by the Hewlett Packard Corporation (Palo Alto, Calif.), and can include or be coupled to a spectrum analyzer, manufactured by the same company.

Referring now to FIGS. 28 and 29, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334. These values can then be displayed at a user interface and display 336. Signals representative of power and impedance values are received by controller 338, which can be a microprocessor.

A control signal is generated by controller 338 that is proportional to the difference between an actual measured value and a desired value. The control signal is used by power circuits 340 to adjust the power output in an appropriate amount in order to maintain the desired power delivered at the respective primary and/or secondary antennas 314 and 316. In a similar manner, temperatures detected at sensors 324 provide feedback for maintaining a selected power. The actual temperatures are measured at temperature measurement device 342, and the temperatures are displayed at user interface and display 338. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensors 324. A multiplexer 346 can be included for measurement of current, voltage, and temperature at the numerous sensors 330, 332 and 324, as well as for delivery and distribution of energy between primary electrodes 314 and secondary electrodes 316. Suitable multiplexers 346 include, but are not limited to, those manufactured by the National Semiconductor Corporation (Santa Clara, Calif.), such as the CLC 522 and CLC 533 series; and those manufactured the Analog Devices Corporation (Norwood, Mass.).

Controller 338 can be a digital or analog controller, or a computer with embedded, resident, or otherwise coupled software. In an embodiment, controller 338 can be a PENTIUM® family microprocessor, manufacture by the Intel Corporation (Santa Clara, Calif.). When controller 338 is a computer, it can include a CPU coupled through a system bus. On this system bus can be a keyboard, a disk drive, or other non-volatile memory systems, a display, and other peripherals, as are known in the art. Also coupled to the bus are a program memory and a data memory. In various embodiments, controller 338 can be coupled to imaging systems, including, but not limited to, ultrasound, CT scanners (including fast CT scanners, such as those manufacture by the imatron Corporation of South San Francisco, Calif.), X-ray, MRI, mammographic X-ray, and the like. Further, direct visualization and tactile imaging can be utilized.

User interface and display 336 can include operator controls and a display. In an embodiment, user interface 336 can be a PDA device known in the art, such as a PALM® family computer, manufactured by Palm Computing (Santa Clara, Calif.). Interface 336 can be configured to allow the user to input control and processing variables to enable the controller to generate appropriate command signals. Interface 336 can also receive real time processing feedback information from one or more sensors 324 for processing by controller 338, to govern the delivery and distribution of energy, fluid, etc.

The outputs of current sensor 330 and voltage sensor 332 are used by controller 338 to maintain a selected power level at primary and secondary antennas 314 and 316. The amount of RF energy delivered controls the amount of power. A profile of power delivered can be incorporated in controller $38, and a preset amount of energy to be delivered can also be profiled.

Circuitry, software, and feedback to controller 338 result in process control and maintenance of the selected power, and are used to change: (i) the selected power, including RF, microwave, laser, and the like, (ii) the duty cycle (on-off and wattage), (iii) bipolar or monopolar energy delivery mode, and (iv) infusion medium delivery, including flow rate and pressure, from infusion source 312. These process variables are controlled and varied to maintain the desired delivery of power, independent of changes in voltage or current, based on temperatures monitored at sensors 324. A controller 338 can be incorporated into feedback control system 329 to switch power on and off, as well as to modulate the power. Also, with the use of sensor 324 and feedback control system 329, tissue adjacent to RF electrodes 314 and 316 can be maintained at a desired temperature for a selected period of time, without causing a shutdown of the power circuit 340 to electrodes 314 and 316 due to the development of excessive electrical impedance at electrodes 314 and 316 or in adjacent tissue.

Referring now to FIG. 29, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage which represents the respective sensed impedances/temperatures. Digitized amplifier output voltages are supplied by A/D converter 348 to a microprocessor 350. Microprocessor 350 may be a Power PC chip available from Motorola, or an INTEL® PENTIUM® Series chip. However, it will be appreciated that any suitable microprocessor, or general purpose digital or analog computer, can be used to calculate impedance or temperature, or perform image processing and tissue identification functions.

Microprocessor 350 sequentially receives and stores digital representations of impedance and temperatures. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with predetermined power and impedance limits. When the values exceed predetermined power or impedance values, a warning can be given on user interface and display 336, and additionally, the delivery of RF energy can be reduced, modified, or interrupted. A control signal from microprocessor 350 can modify the power level supplied by energy source 320 to RF electrodes 314 and 316. In a similar manner, temperatures detected at sensors 324 provide feedback for determining the extent and rate of: (i) tissue hyperthermia, (ii) cell necrosis; and (iii) when a boundary of desired cell necrosis has reached the physical location of sensors 324.

Figure 30:
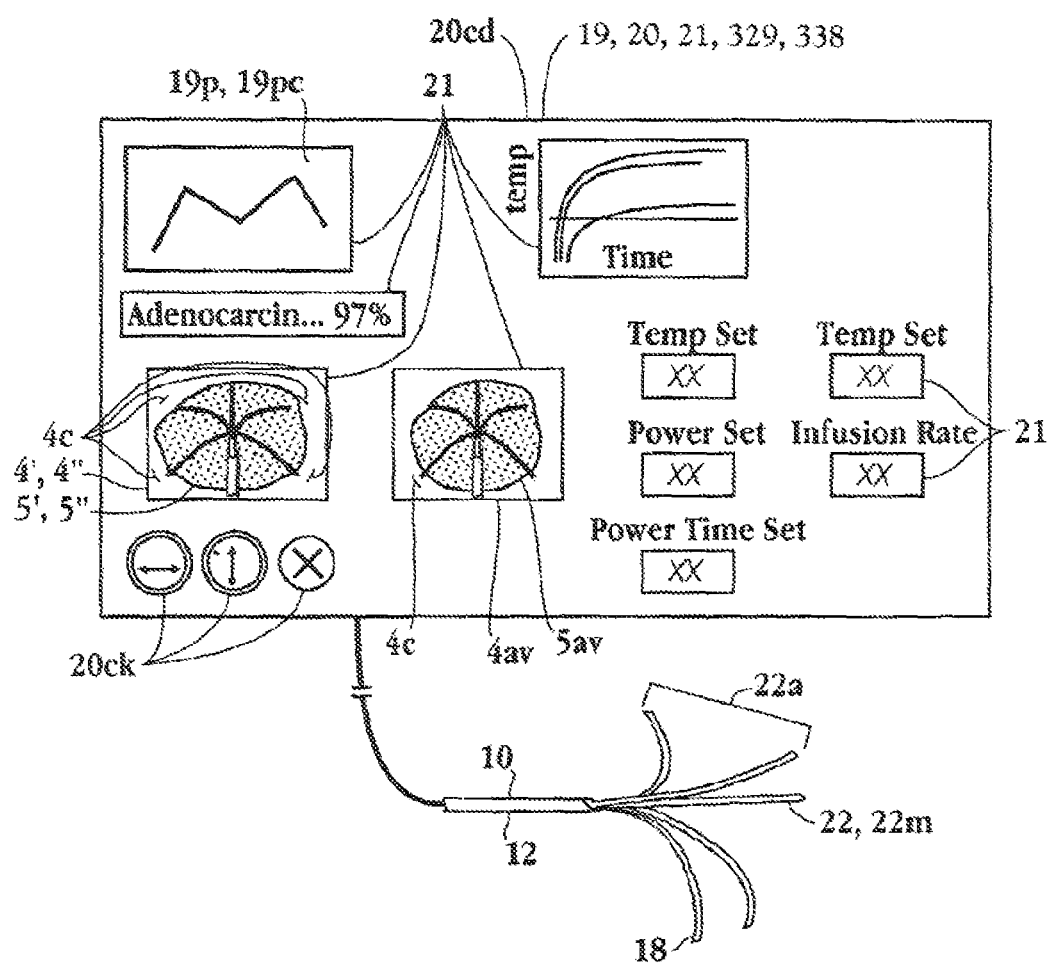
FIG. 30 is a lateral view illustrating a control and display unit.

Referring now to FIG. 30, in an embodiment, one or more of impedance measurement device 19, power supply 20, display device 21, control system 329, controller 338 can be incorporated or integrated into a single control and display device or unit 20cd. Device 20cd can be configured to include displays for one or more of the following: impedance profile 19p, tissue site image 4', tumor volume image 4", ablation volume image 4av, time-temperature profiles, tissue identification information, and ablation setting information (e.g. power setting, delivery time, etc.). Device 20cd can also be configured to superimpose ablation volume image 4av onto tumor volume image 4" or tissue site image 4', as well as to superimpose visual cues 4c on the placement (including proper and improper placement) of apparatus 10 (including energy delivery devices 18) within the tumor volume 5" or tissue site 5'. Device 20cd can also include controls 20ck for manipulating any of the images (4', 4" or 4av) in one or more axis.

Figure 31:
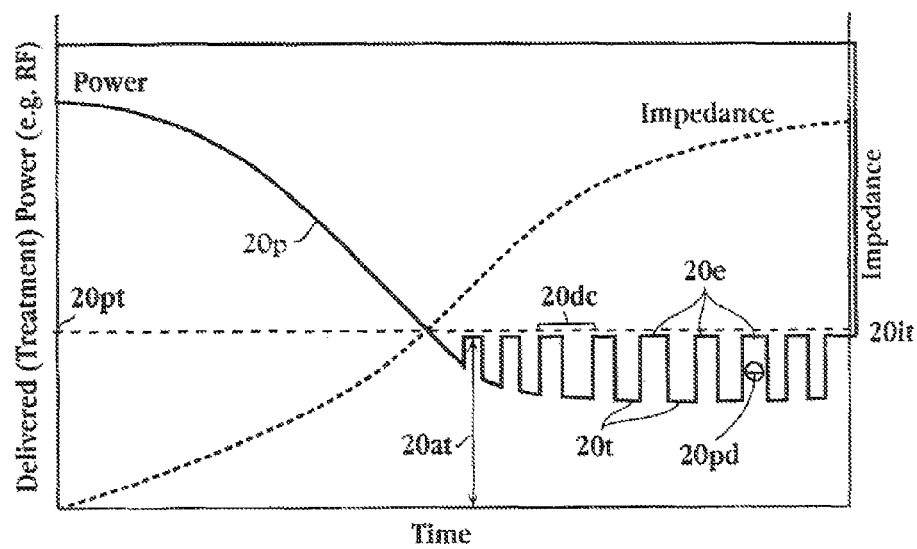
FIG. 31 is a plot showing an impedance measurement duty cycled signal superimposed on an RF treatment signal under selectable threshold conditions.

Referring now to FIG. 31, in various embodiments, impedance measurement device 19 or control system 329 can be configured to switch from a first mode of measuring impedance to a second mode, when certain system impedance or power conditions occur. In an embodiment, the first mode of measuring impedance is done utilizing the RF treatment power, and then impedance is calculated using a measured current and voltage as described herein. However, when system impedance rises too greatly and the resulting RF power treatment power level drops below a threshold, the accuracy and precision of localized impedance measurements decreases as a result of the decrease in the impedance measurement current in relation to noise levels of the RF power system. This is a problem not recognized nor addressed by current RF ablative and related impedance measurement devices. Under such conditions, logic resources 19lr within monitoring device 19 can be configured to switch to a second mode of measuring localized impedance. The threshold event causing the mode switching can be selectable, and include one or more of the following events, decreases in treatment (e.g. RF) power below a threshold level 20pt, increases in system impedance above a threshold level 20it, changes in slope (e.g. derivative) of the RF power or system impedance curves. In various embodiments, the threshold level 20pt of RF treatment power 20p causing mode switching can be in the range from 1 to 50 watts, with specific embodiments of 5, 10 and 25 watts.

In an embodiment, shown in FIG. 31, the second or alternative mode of measuring impedance can comprise superimposing a duty cycled measurement signal 20e onto the treatment signal 20t. The pulse duration 20pd of signal 20e can be in the range of 1 to 500 ms, with specific embodiments of 50, 100 and 250 ms. The duty cycle 20dc of signal 20e can be in the range from 1 to 99%, with specific embodiments of 10, 25, 50 and 75%. Monitoring device 19, power source 20, or control system 329 can be configured to control the power amplitude of the measurement signal 20e to maintain a selected total amplitude 20at. In an embodiment, the total power amplitude 20at can range from about 5 to about 50 watts, with specific embodiments of 10, 20, 30 and 40 watts. Also, the duty cycle, pulse duration, and total power amplitude can be controlled to deliver a selectable average power over the duty cycle, which can be in the range of about 0.5 to about 10 watts, with specific embodiments 1, 2, 5 and 5 watts. By controlling the average power delivered over the duty cycle, higher measurement currents 20e can be used in short pulse duration without appreciably affecting delivered treatment power or system performance, or causing additional or unwanted energy delivery to the target tissue site. In use, these and related embodiments of alternative mode of impedance measurements (including superimposed duty cycle measurement) provide the benefit of improved accuracy and signal to noise ratios of impedance and related bio-electric measurements under conditions of high system impedance and/or low levels of delivered RF treatment power (i.e. ablative power).

In related embodiments, the duty cycle and/or pulse duration can be configured to vary responsive to one or more selected parameters, which can include frequency of the treatment signal, power for the treatment signal, or tissue impedance to the treatment signal. The variation in either the pulse duration or duty cycle can be controlled by control system 329 and/or logic resources 19lr of the impedance monitoring device 19 or power supply 20, using control methods known in the art, such as PID control. In use, these embodiments allow the impedance measurements to be continuously fine tuned to changing system conditions to improve the accuracy and precision of impedance and related bioelectric measurements.

The foregoing description of various embodiment of the application has been presented for purposes of illustration and description. It is not intended to be exhaustive or to limit the application to the precise forms disclosed. Embodiments of the application can be configured for the treatment of tumor and tissue masses at or beneath a tissue surface in a number of organs, including, but not limited to, the liver, breast, bone and lung. However, embodiments of the application are applicable to other organs and tissues as well. Obviously, many modifications and variations will be apparent to practitioners skilled in this art. Further, elements from one embodiment can be readily recombined with elements from one or more of other embodiments. Such combinations can form a number of embodiments within the scope of the application. It is intended that the scope of the application be defined by the following claims and their equivalents.

The invention claimed is:

1. A method of ablating a tissue tract, comprising:
providing an energy delivery member configured for insertion into a target tissue;
inserting the delivery member into an insertion site;
advancing the delivery member thereby forming a tissue tract, extending from the insertion site to the target tissue, substantially five of tumor cells;
delivering energy sufficient to ablate substantially all tumor cells in the target tissue;
withdrawing the delivery member along the formed tissue tract; and
delivering energy to at least a portion of the formed tissue tract.

2. The method of claim 1, wherein the method further comprises delivering electrical energy in the form of electrical pulses sufficient to electroporate substantially all tumor cells along the formed tract while leaving tissue surrounding the tumor cells substantially unchanged.

3. The method of claim 1, wherein the method farther comprises delivering radiofrequency energy during the step of delivering energy sufficient to ablate substantially all tumor cells in the target tissue.

4. The method of claim 1, wherein the method further comprises delivering microwave energy during the step of delivering energy sufficient to ablate substantially all tumor cells in the target tissue.

5. The method of claim 1, wherein the method farther comprises delivering laser energy during the step of delivering energy sufficient to ablate substantially all tumor cells in the target tissue.

6. The method of claim 1, wherein the method further comprises selectively delivering varying amounts of energy to different portions of the tissue tract during the step of delivering, energy sufficient to ablate substantially all tumor cells in the target tissue.

7. The method of claim 1, wherein the method further comprises ablating substantially all tumor cells that are present along the tissue tract.

8. The method of claim 1, wherein the method further comprises delivering energy in the form of electrical energy in a monopolar mode during the step of delivering energy sufficient to ablate substantially all tumor cells in the target tissue.

9. The method of claim 1, wherein the method further comprises delivering energy in the form of electrical energy in a bipolar mode during the step of delivering energy sufficient to ablate substantially all tumor cells in the target tissue.

10. The method of claim 1, wherein the method farther comprises monitoring and altering the delivery of the energy to the tissue tract during the step of delivering energy to ensure that no living malignant tissue is re-seeded along the tract upon withdrawal of the energy delivery device.

11. The method of claim 1, wherein the method further comprises continuously withdrawing the energy delivery device along the tissue tract while delivering energy to at least a portion of the formed tissue tract.

12. The method of claim 1, wherein the method further comprises delivering a fluid to the tissue tract.

13. The method of claim 1, wherein the method further comprises removing aspirated tissue from the tissue tract.

14. The method of claim 3, wherein the method further comprises delivering radiofrequency energy during the step of delivering energy sufficient to ablate at least a portion of the formed tissue tract.

15. The method of claim 4, wherein the method further comprises delivering microwave energy during the step of delivering energy sufficient to ablate at least a portion of the formed tissue tract.

16. The method of claim 5, wherein the method further comprises delivering laser energy during the step of delivering energy sufficient to ablate at least a portion of the formed tissue tract.

17. The method of claim 1, wherein the step of delivering energy sufficient to ablate substantially all tumor cells in the target tissue further includes controlling the energy level with at least one logic resource.

18. The method of claim 17, wherein the logic resource controls the energy level based on measurement of impedance.

19. The method of claim 1, further comprising the step of monitoring the localized impedance.

20. The method of claim 1, further comprising using an ablation monitoring module to determine an ablation endpoint by monitoring an impedance of the target tissue.

21. The method of claim 20, wherein the ablation monitoring module determines the ablation endpoint by using impedance measurements made at multiple frequencies.

22. The method of claim 20, wherein the ablation monitoring module determines the ablation endpoint by comparing at least two impedance curves made at different frequencies.

23. The method of claim 1, wherein delivering energy to at least a portion of the thrilled tissue tract includes directing, to the tissue tract, an ablation energy which is higher than the ablation energy directed to the target tissue.

24. The method of claim 1, further comprising delivering cooling fluid to a lumen of the energy delivery member.

25. The method of claim 24, wherein the delivery of cooling fluid is controlled by a controller.

* * * * *

UNITED STATES PATENT AND TRADEMARK OFFICE
CERTIFICATE OF CORRECTION

PATENT NO. : 8,540,710 B2  
APPLICATION NO. : 13/609369  
DATED : September 24, 2013  
INVENTOR(S) : Theodore C. Johnson, Daniel J. Balbierz and Robert M. Pearson Page 1 of 1

It is certified that error appears in the above-identified patent and that said Letters Patent is hereby corrected as shown below:

In the Claims:

Column 30, line 52, replace "five" with --free--.

Signed and Sealed this  
Nineteenth Day of November, 2013

Teresa Stanek Rea  
*Deputy Director of the United States Patent and Trademark Office*